US008001845B2

(12) United States Patent
Caulfield et al.

(10) Patent No.: US 8,001,845 B2
(45) Date of Patent: Aug. 23, 2011

(54) GYRATORY COMPACTOR APPARATUSES AND ASSOCIATED METHODS

(75) Inventors: Francis D. Caulfield, Raleigh, NC (US); Raffaello Verna, Creedmoor, NC (US); Thomas Brovold, Barnes, WI (US); Francois J. Malassenet, Raleigh, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

(21) Appl. No.: 12/685,482

(22) Filed: Jan. 11, 2010

(65) Prior Publication Data
US 2010/0281995 A1 Nov. 11, 2010

Related U.S. Application Data

(60) Provisional application No. 61/143,529, filed on Jan. 9, 2009.

(51) Int. Cl.
*G01N 3/08* (2006.01)
(52) U.S. Cl. .................. 73/824; 72/818; 72/825
(58) Field of Classification Search ............... 73/818, 73/824, 825
See application file for complete search history.

(56) References Cited

U.S. PATENT DOCUMENTS

| | | | |
|---|---|---|---|
| 5,323,655 A | 6/1994 | Eagan et al. | |
| 5,394,753 A * | 3/1995 | Moriyoshi | 73/818 |
| 5,456,118 A | 10/1995 | Hines et al. | |
| 5,606,133 A | 2/1997 | Hines et al. | |
| 5,817,946 A | 10/1998 | Brovold | |
| 5,824,913 A | 10/1998 | Pyle | |
| 5,916,504 A * | 6/1999 | Edwards et al. | 264/71 |
| 5,939,642 A | 8/1999 | King et al. | |
| 6,026,692 A * | 2/2000 | Brovold | 73/818 |
| 6,477,783 B1 | 11/2002 | Harman et al. | |
| 6,729,189 B2 * | 5/2004 | Paakkinen | 73/824 |
| 6,868,738 B2 * | 3/2005 | Moscrip et al. | 73/818 |
| 6,889,558 B2 | 5/2005 | Hines | |
| 6,925,889 B2 | 8/2005 | Pyle et al. | |
| 7,121,149 B2 | 10/2006 | Verna et al. | |
| 7,360,444 B2 | 4/2008 | Verna et al. | |
| 7,370,574 B2 | 5/2008 | Verna et al. | |
| 2003/0089178 A1 * | 5/2003 | Paakkinen | 73/818 |

(Continued)

OTHER PUBLICATIONS

PCT International Search Report, Sep. 27, 2010.

(Continued)

*Primary Examiner* — Lisa Caputo
*Assistant Examiner* — Jonathan Dunlap
(74) *Attorney, Agent, or Firm* — Olive Law Group, PLLC

(57) ABSTRACT

A gyratory compactor apparatus is provided that is adapted to interact with a mold that defines a mold axis. The gyratory compactor apparatus includes a frame that defines a frame axis and has a first mounting plate and a spaced-apart second mounting plate. A pivoted support is carried by the frame and capable of rotation in at least a first and a second rotational degree of freedom. A mold-engaging device is carried by the pivoted support and has a first carriage plate proximal the pivoted support and a second carriage plate axially spaced-apart from the pivoted support for receiving the mold therebetween. At least one actuator having a first end is carried by the frame and a second end is carried by the second carriage plate for imparting lateral translation to the second carriage plate relative to the frame axis. An associated method is also provided.

34 Claims, 17 Drawing Sheets

U.S. PATENT DOCUMENTS

| | | | |
|---|---|---|---|
| 2004/0020306 A1* | 2/2004 | Moscrip et al. | 73/824 |
| 2004/0079166 A1* | 4/2004 | Moscrip et al. | 73/824 |
| 2004/0194552 A1* | 10/2004 | Verna et al. | 73/824 |
| 2005/0022608 A1* | 2/2005 | Moscrip | 73/818 |
| 2007/0017298 A1* | 1/2007 | Verna et al. | 73/818 |
| 2007/0017299 A1* | 1/2007 | Verna et al. | 73/818 |
| 2010/0281945 A1* | 11/2010 | Caulfield et al. | 73/1.77 |
| 2010/0288053 A1* | 11/2010 | Caulfield et al. | 73/818 |

OTHER PUBLICATIONS

Notification of Transmittal of the International Search Report and the Written Opinion of the International Searching Authority, or the Declaration, Korean Intellectual Property Office, dated Sep. 27, 2010 (Cited in relation to corresponding PCT international application).

* cited by examiner

GYRATORY COMPACTOR APPARATUSES AND ASSOCIATED METHODS

CROSS REFERENCE TO RELATED APPLICATION

This application claims priority to U.S. Provisional Patent Application No. 61/143,529, filed on Jan. 9, 2009, the content of which is incorporated herein in its entirety. The disclosures of the following United States Utility Patent Applications, commonly owned and simultaneously filed herewith, are all incorporated by reference in their entirety: GYRATORY COMPACTOR APPARATUSES AND ASSOCIATED METHODS Ser. No. 12/685,498; and CALIBRATION OF GYRATORY COMPACTOR APPARATUSES AND ASSOCIATED METHODS Ser. No. 12/685,519.

TECHNICAL FIELD

The presently disclosed subject matter relates to gyratory compactor apparatuses and associated methods. More particularly, the presently disclosed subject matter relates to improved gyratory compactor apparatuses and associated devices and methods.

BACKGROUND

In order to measure certain physical properties, such as density, moisture content and compressive strength of some materials such as soil or paving material, loose samples of the soil or paving material are formed into test specimens under reproducible conditions using laboratory compaction machines. In order to replicate actual expected conditions, it is desirable to compact the test specimens under conditions that simulate actual use. For a paving material sample, this requires simulation of the kneading force applied to the paving material by a paving roller, such as rollers with smooth or sheeps/pad-foot drums or pneumatic wheels, or vibratory compactors such as those used in intelligent compaction. Simply applying a compressive force to the sample does not adequately simulate the kneading action of the paving roller, as the paving roller also applies a shear force to the material being compacted. As a result, compaction machines that apply an orbital motion to the paving sample during compression have been developed to simulate actual conditions of use. For simplicity of implementation and analysis, the orbital motion in many current compaction machines has been restricted to gyration along a circular orbit.

The combination of shear and compaction effort applied to the gyrating specimen is designed to mimic the kneading effect of in-situ compaction of a material using a rolling compactor. Typically, the gyration of the mold is performed with an offset so that the axis of the mold is at an angle from the compression force from the ram. The corresponding average angle between the direction of the compression force and the position of the mold axis is often referred to as the internal angle.

This internal angle is the angle of applied confinement forces with respect to the main axis of rotation that the specimen is really subject to. Its measurement and calibration is typically performed using a self-contained device such as the Rapid Internal Angle Measurement (RAM) unit, an example of which is disclosed in U.S. Pat. No. 6,925,889, or Dynamic Angle Validator (DAV), an example of which is disclosed in U.S. Pat. No. 6,477,783B1. These devices are shear force simulation devices that mimic the shear effort applied to a material and have the capability to also measure, store, and display the internal angle by way of difference of distance measurement of the position of the inside of the mold with respect to the perpendicular direction to a mold plate. A simple way to infer the internal angle applied to the sample material is to measure the external angle, i.e., the angle between the reference frame and the mold. However, when forces are applied to the frame and the mold, the frame can flex, the ram position and direction of force can vary, and the corresponding perpendicular direction of the mold plates can change with respect to the inside axis of the mold. These are not the exhaustive list of factors that can affect the actual internal angle versus the measured internal angle. They are, however, the main variables that can make the relationship between internal angle and external angle vary in time between the top and bottom of the sample.

Various disadvantages have been associated with previously developed gyratory compactors. For example, some gyratory compactors include a ram applying compressive force from one end of a cylindrical mold, while the other end of the mold is gyrated by rotating a base supporting the other end of the mold. However, these machines could not easily determine and maintain a consistent angle of gyration due to inconsistencies during rotation of the base supporting the other end of the mold and flexure of the gyratory compactor during operation. Most implementations included the use of a mechanical interference to constrain the shape of the gyration motion.

Another example of a gyratory compactor apparatus is disclosed in U.S. Pat. No. 5,939,642 to King et al. (the '642 patent). The '642 patent describes a gyratory compactor apparatus design for facilitating ergonomics and efficiency, while improving consistency of operating parameters. The gyratory compactor described therein allows the user to slide the cylindrical compaction mold into the compaction chamber without the necessity of lifting the mold. In addition, the compactor of the '642 patent includes an integral specimen removal ram, which facilitates easy removal of the specimen from the mold. In addition, the frame design reduces frame deflection that could undesirably affect the angle of gyration. Further, the angle of gyration of the compactor apparatus can be changed by simply replacing a single component of the apparatus. Notwithstanding the advances that have been made in the art of gyratory compactors, there is a need for smaller and less costly designs, with improved operational efficiency and accuracy. Additionally, there is a need for a gyratory compactor having improved ergonomics. For example, placement and removal of the mold containing the sample should be accomplished with minimal difficulty. Additionally, it would be desirable to produce a lightweight frame design that also minimizes frame flexure, thus providing more accurate test results. Moreover, it would be advantageous to enable release of water content when the sample material is fully or partially saturated soil or emulsified asphalt. Also, it would be advantageous to provide a compactor design that allows the user to quickly, easily, dynamically, and/or in real-time change, control, and calibrate operating parameters, such as the angle of gyration, shape of gyration, and ability to control applied axial load. Further, there is a need in the art for a gyratory compactor that provides a constant, precise, and accurate internal angle of gyration during the compaction procedure with minimal deviation therefrom.

SUMMARY

According to one aspect, a gyratory compactor apparatus is provided. The compactor apparatus is adapted to interact with a mold that defines a mold axis. The gyratory compactor apparatus includes a frame defining a frame axis and having a first mounting plate and a spaced-apart second mounting plate and a pivoted support carried by the frame and capable of rotation in at least a first and a second rotational degree of freedom. A mold-engaging device is carried by the pivoted support and has a first carriage plate proximal the pivoted support and a second carriage plate axially spaced-apart from the pivoted support for receiving the mold therebetween. The second carriage plate is laterally moveable relative to the frame axis by rotation of the pivoted support in either of the first or second degrees of freedom. At least one actuator having a first end carried by the frame and a second end carried by the second carriage plate for imparting lateral translation to the second carriage plate relative to the frame axis is provided. A gyratory internal angle is defined between the frame axis and the mold axis.

According to another aspect, the second carriage plate is axially translatable about the mold axis.

According to another aspect, the mold-engaging device is slideably carried by the pivoted support.

According to another aspect, the mold-engaging device further includes an actuator for providing clamping forces to the mold-engaging device and imparting axial translation of the second carriage plate.

According to another aspect, the pivoted support is a gimbal.

According to another aspect, the compactor apparatus also includes a ram rod in generally axial alignment with the frame axis for providing rotational movement and compressive forces to the mold about the frame axis.

According to another aspect, the compactor apparatus also includes a position sensor in communication with the ram rod.

According to another aspect, the compactor apparatus also includes an anti-rotate plate on a distal end of the ram rod and further including a plurality of spaced-apart support beams carried on a first end about a periphery of the anti-rotate plate and carried on a second end at the second mounting plate for providing torsional rigidity to retard torsional strain imparted from rotation of the ram rod.

According to another aspect, each actuator of the at least one actuator is a hydraulic actuator.

According to another aspect, each actuator of the at least one actuator is independently controlled relative to each other actuator.

According to another aspect, the compactor apparatus also includes a displacement measurement device in communication with each actuator of the at least one actuator for measuring displacement of each actuator.

According to another aspect, each of the at least one actuators define a longitudinal axis between the first end and the second end of each actuator, and an actuation angle is formed relative to the longitudinal axis of each actuator and the frame axis, and wherein the actuation angle is about 23 degrees.

According to another aspect, each actuator of the at least one actuator is carried by the first mounting plate.

According to another aspect, the mold is a mold of the type having an elongate cylinder that defines a cavity therein for receiving the sample.

According to another aspect, the mold is of the type having a peripherally extending flange extending from the cylinder at a first end and a second end thereof.

According to another aspect, an alternate embodiment of gyratory compactor apparatus adapted to interact with a mold that defines a mold axis is provided. The gyratory compactor apparatus includes a frame having a first mounting plate and defining a frame axis extending from the first mounting plate, a pivoted support carried by the frame, a first carriage plate moveable in response to movement of the pivoted support, and a second carriage plate spaced-apart from the first carriage plate, the second carriage plate being attached to the first carriage plate by at least one clamping rod extending therebetween. A ram rod is in general alignment with the second carriage plate for providing compressive and gyratory forces to a mold held between the first and second carriage plates. At least one actuator carried on a first end by the frame and on a second end by the second carriage plate is provided. The actuator is operable to offset the second carriage plate relative to the frame axis such that during gyration of the mold. This offset defines a gyratory internal angle between the frame axis and the mold axis.

According to another aspect, the gyratory compactor apparatus includes a mold-engaging device that is slideably carried by the pivoted support.

According to another aspect, the at least one actuator that imparts axial translation applies a predetermined axial load or force and corrects the internal angle accordingly.

According to another aspect, the mold engaging device also includes a translation mechanism for imparting axial translation of and providing clamping forces to the second carriage plate.

According to another aspect, a method for testing a sample contained within a mold for a gyratory compactor apparatus is provided. The gyratory compactor apparatus has a frame that carries a mold-engaging device having a pivoted support, a first carriage plate moveable in response to movement of the pivoted support, a second carriage plate spaced-apart from the first carriage plate for receiving the mold therebetween, and at least one actuator carried on a first end by the frame and on a second end at the second carriage plate. The method includes the steps of placing a mold in engagement with the mold-engaging device, rotating the mold, and then imparting lateral displacement of the mold relative to the frame axis by actuation of the at least one actuator to thereby define a gyratory internal angle between the frame axis and the mold axis.

According to another aspect, the gyratory compactor apparatus further includes a ram rod in general alignment with the mold for compacting the mold, and the method also includes the step of compacting the mold with the ram rod.

According to another aspect, the gyratory compactor apparatus includes the step of measuring the compaction of the compacted material in the mold.

According to another aspect, the mold is rotated about the ram rod.

According to another aspect, the method also includes the step of measuring the gyratory angle. The internal angle can be directly measured using sensors or devices such as a DAV, RAM, or at least one inclinometers in operational relation with at least one of internal or external lateral surfaces of the mold.

According to another aspect, the method also includes the step of calibrating the angle. The calibration step includes the step of inferring the position or length of at least one of the actuators into an external angle. This external angle and the compressive force applied to the sample material to be included to calibrate the internal angle that is actually perceived by the sample under test. The calibration process can use a moment simulation device and/or internal angle measurement device such as a RAM unit or a DAV.

According to another aspect, the method also includes the step of measuring the at least one internal or external radial forces. The measurement of the at least one direction of the forces can be done directly by way of at least one force, pressure or load sensor that can be selected from mechanical, optical, electrical, piezoelectric, electromechanical sensors such load cells, pressure transducers, calibrated displacement measurement transducers, energy dissipation and the like. The transducers monitor at least one of the transducers and/or the ram head, and/or the clamping devices.

According to another aspect, the method also includes the step of controlling the at least one internal or external radial forces applied to the sample material. This step can take into account the anisotropic behavior of the overall gyratory assembly flexure under different compressive pressures applied to the sample, wherein varying compressive forces and structural rigidity causes anisotropic behavior of flexure of the gyratory compactor apparatus. Examples of cause and location of flexures include and are not limited to actuator, gimbal, frame, plate assemblies, ram head and/or shaft flexures.

According to another aspect, the method also includes the step of applying a predetermined moment on the sample material. The moment may be constant in time, varying in time, with or without a periodic component. Once the predetermined moment is applied, the method may include the control of the angle inducing the corresponding eccentricity.

According to another aspect, the method also includes the step of applying a predetermined moment on the sample material. The moment may be continuous in time, varying in time, with or without a periodic component.

According to another aspect, the measurement of the gyratory internal angle is measured instantaneously for each rotation of the mold relative to each rotation of the mold. The measurement of the gyratory angle may also be averaged for each rotation of the mold. The measurement can be performed directly without limitation by at least one inclinometer operative to the inside or outside of the mold or an angle measurement device such as the RAM/DAV, or the measurement can be performed indirectly by the location of at least one of the carriage plate assemblies or the position of at least one actuator lengths. These measurements can be taken continuously or at least one predetermined position in the orbit of the motion, or at least one predetermined time of operation including at predetermined intervals of times.

According to another aspect, in the step of imparting lateral displacement of the mold relative to the frame axis by actuation of the at least one actuator, the at least one actuator is a hydraulic actuator in communication with a hydraulic source.

According to another aspect, the vertical force applied to the sample material is modeled to a predetermined waveform. The user can select the characteristic of the waveform including and not limited to the shape such as sinusoidal, triangular and the parameters associated with such waveform, including but not limited to the amplitude, phase, offset, dynamic range, time delay, and other various parameters.

According to another aspect, a gyratory compactor apparatus is provided that is adapted to interact with a mold defining a mold axis. The gyratory compactor apparatus includes a ram rod in generally axial alignment with the mold axis for providing compressive forces to the mold about the mold axis. The compressive forces provided by the ram rod to the mold models a predetermined waveform.

According to another aspect, the waveform is a sinusoidal waveform.

According to another aspect, the waveform is a triangular waveform.

According to another aspect, the waveform is a saw-tooth waveform.

According to another aspect, the waveform is a square waveform.

According to another aspect, the apparatus also includes a signal generator in communication with the ram rod for providing the predetermined waveform.

According to another aspect, a method for compacting a sample contained within a mold for a gyratory compactor apparatus is provided. The gyratory compactor apparatus is of the type having a mold-engaging device and includes the steps of placing the mold in engagement with the mold-engaging device and imparting compressive forces to the mold in order to compact the sample contained therein. The compressive forces are imparted according to a predetermined waveform.

According to another aspect, a gyratory compactor apparatus is provided that is adapted to interact with a mold that defines a first end and a spaced-apart second end. The gyratory compactor apparatus includes a mold-engaging device having a carriage plate assembly for engaging a respective one of the first or second ends of the mold. The carriage plate assembly has a first engagement surface for engaging the respective one of the first or second ends of the mold. At least one of the first engagement surface, the first end of the mold, or the spaced-apart second end of the mold includes at least one textural feature for providing anti-slip characteristics between the first engagement surface and the respective one of the first or second ends of the mold.

According to another aspect, the textural feature comprises at least one groove.

According to another aspect, the textural feature comprises etching.

According to another aspect, the textural feature comprises chiseling.

According to another aspect, the textural feature comprises sandblasting.

According to another aspect, the textural feature comprises a friction increasing coating.

According to another aspect, the first engagement surface defines a textural feature.

According to another aspect, the first end of the mold defines a textural feature.

According to another aspect, the spaced-apart, second end of the mold defines a textural feature.

According to another aspect, the carriage plate assembly includes a second engagement surface spaced-apart from the first engagement surface which defines a space therebetween for receiving the mold. The second engagement surface engages the other of the respective one of the first or second ends of the mold.

According to another aspect, the second engagement surface defines a textural feature.

According to another aspect, the first engagement surface includes a textural feature and the first end of the mold includes a textural feature. The textural feature of the first engagement surface and the textural feature of the respective one of the first or second ends of the mold are configured to matingly engage and thereby increase axial friction at the engagement of the first engagement surface and the respective one of the first or second ends of the mold.

According to another aspect, the mold is a mold of the type having an elongate cylinder that defines a cavity therein for receiving the sample, and having a peripherally extending flange extending from the cylinder at a first end and a second end thereof.

According to another aspect, the mold is a mold of the type having an elongate cylinder that defines a cavity therein for receiving the sample, and the mold does not have a peripherally extending flange extending from the cylinder at a first end and a second end thereof.

According to another aspect, the mold is a mold of the type consisting of an elongate cylinder that defines a cavity therein for receiving the sample.

According to another aspect, a method for calibrating a gyratory compactor apparatus is provided. The gyratory compactor apparatus is of the type being configured to compact and impart an orbital motion to a sample in a mold that defines a mold axis and includes at least one actuator for imparting lateral displacement of the mold relative to a longitudinal axis of the gyratory compactor apparatus. The method includes the steps of imparting lateral orbital displacement of the mold relative to the gyratory compactor apparatus by actuation of the at least one actuator to thereby define a gyratory angle between the gyratory compactor apparatus and the mold axis, measuring the gyratory angle, and determining adjustments to actuation of the at least one actuator based on the measured gyratory angle and a target angle.

According to another aspect, the method also includes the step of measuring a force exerted on the mold, and wherein determining adjustments to actuation comprises determining adjustments to actuation of the at least one actuator based on the measured force.

According to another aspect, in the step of measuring the gyratory angle, the step includes measuring the gyratory angle relative to each rotation of the mold.

According to another aspect, in the step of imparting lateral orbital displacement, the step includes imparting lateral orbital displacement of the mold relative to the gyratory compactor apparatus by actuation of a hydraulic actuator in communication with a hydraulic source.

According to another aspect, a gyratory compactor apparatus is provided. The gyratory compactor apparatus is of the type being adapted to interact with a mold that defines a mold axis and includes at least one actuator configured to impart lateral orbital displacement of the mold relative to the gyratory compactor apparatus to thereby define a gyratory angle between the gyratory compactor apparatus and the mold axis. A control system is provided and is configured to determine adjustments to actuation of the at least one actuator based on a measurement of the gyratory angle and a target angle control actuation of the at least one actuator based on the determined adjustments.

According to another aspect, the gyratory compactor apparatus includes a force sensor configured to measure a force exerted on the mold. The control system is configured to determine adjustments to actuation of the at least one actuator based on the measured force.

According to another aspect, each actuator of the at least on actuator is independently controlled by the control system.

According to another aspect, each actuator of the at least one actuator is a hydraulic actuator.

According to another aspect, a method for calibrating a gyratory compactor apparatus configured to compact and impart a displacement to a sample in a mold that defines a mold axis is provided. The gyratory compactor apparatus includes at least one actuator for imparting lateral displacement of the mold relative to a longitudinal axis of the gyratory compactor apparatus. The method includes the steps of inserting a moment simulation device in a mold to apply a predetermined moment, imparting lateral displacement of the mold relative to the gyratory compactor apparatus by actuation of the at least one actuator to thereby define a gyratory angle between the gyratory compactor apparatus and the mold axis, measuring the actual moment, applying a compression force onto the mold to thereby generate an actual moment, measuring at least one force applied by the at least one actuator, and determining a relationship between the measured at least one force applied by the at least actuator and the applied moment.

According to another aspect, the method includes the step of determining a corrective parameter for the moment simulation device based on the determined relationship.

According to another aspect, the method includes the step of storing the corrective parameter.

According to another aspect, the method includes the step of filtering the measurement of the at least one force.

According to another aspect, the method includes the step of displaying the measurement of the actual moment.

According to another aspect, the method includes the step of interpolating and extrapolating at least one correction for different predetermined forces exerted on the mold.

According to another aspect, a gyratory compactor apparatus adapted to compact and impart an orbital motion to a sample in a mold that defines a mold axis is provided. The gyratory compactor apparatus includes at least one actuator configured to impart lateral orbital displacement of the mold relative to the gyratory compactor apparatus to thereby define a gyratory angle between the gyratory compactor apparatus and the mold axis, a device configured to apply a compression force onto the mold, and at least one sensor configured to measure at least one force applied by the at least one actuator. A control system is provided that is configured to control the gyratory compactor apparatus to vary the orbital motion to match a predetermined moment to be exerted on the sample.

According to another aspect, the control system is configured to determine a corrective parameter for the moment simulation device.

According to another aspect, the control system is configured to store the corrective parameter.

According to another aspect, the control system is configured to filter the measurement of the at least one force.

According to another aspect, the gyratory compactor apparatus further includes a display configured to display the measurement of the actual moment.

According to another aspect, the gyratory compactor apparatus further includes a display configured to display one of error of the measurement of the actual moment from a target moment, a three-dimensional representation of the actual moment, shear pressure, shear moment, eccentricity, eccentricity vector, or any other information related to moments, passing or failing criteria of target moment information.

According to another aspect, the gyratory compactor apparatus further includes a display configured to display one of the measurement of the actual angle or corresponding error from the prescribed value, the three-dimensional representation of the angle, and average angle per gyration.

According to another aspect, the gyratory compactor apparatus further includes a memory configured to store one of the measurement of the actual angle or corresponding error from the prescribed value, the three-dimensional representation of the angle, and average angle per gyration.

According to another aspect, the control system is configured to interpolate and extrapolate at least one correction for different predetermined forces exerted on the mold.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings.

DETAILED DESCRIPTION

Figure 1:
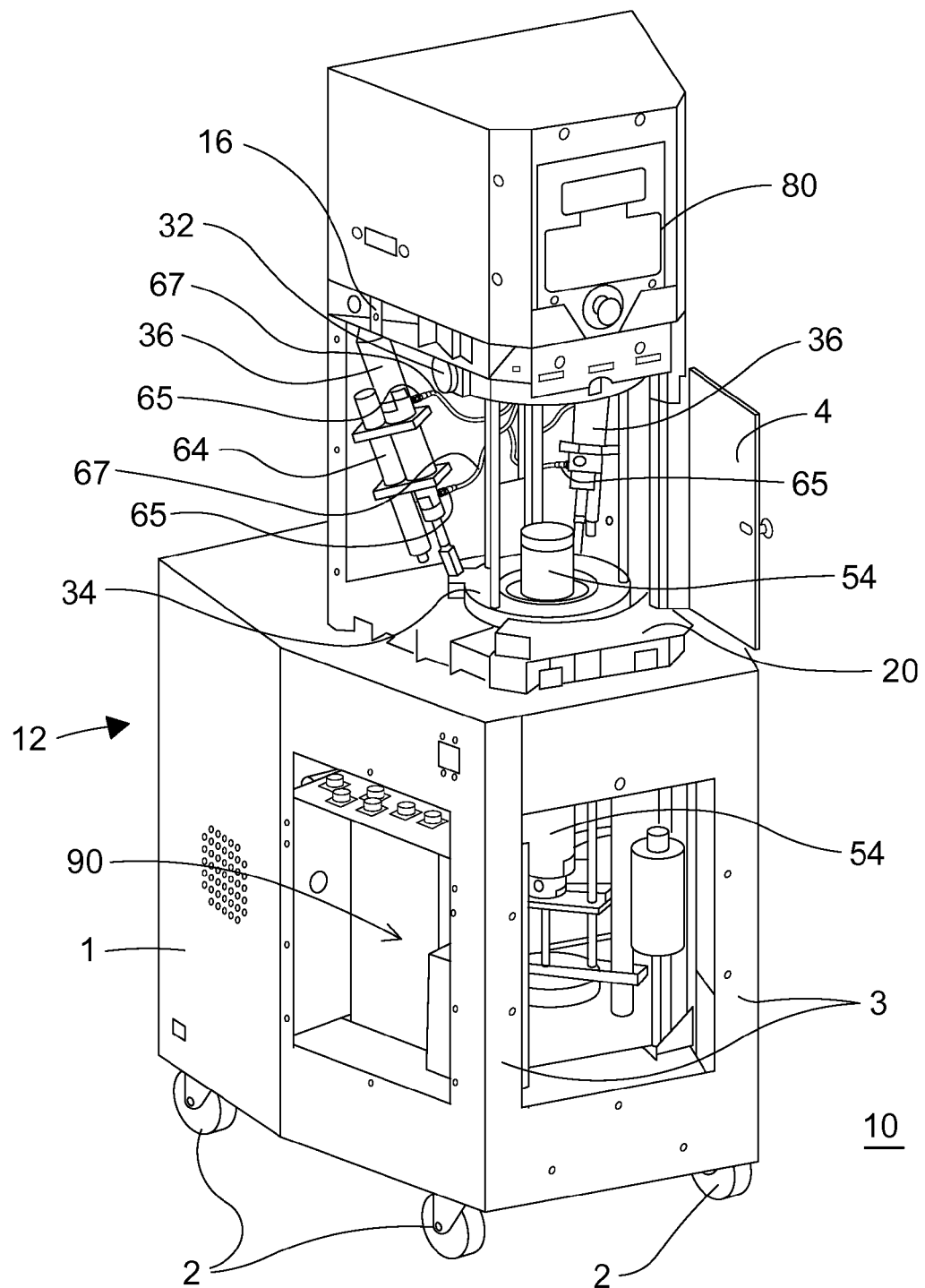
FIG. 1 is a perspective view of a gyratory compactor apparatus according to an embodiment of the presently disclosed subject matter.

The presently disclosed subject matter now will be described more fully hereinafter with reference to the accompanying drawings, in which some, but not all embodiments are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

A gyratory compactor apparatus is shown throughout the Figures and is generally designated 10. The gyratory compactor apparatus 10 broadly includes a cart 1 with a plurality of wheels 2 attached thereto for providing rolling movement of the cart 1 over a floor. A plurality of upright supports 3 add increased structural integrity to the cart 1 and define openings therebetween for providing access to various components of the gyratory compactor apparatus 10. A hinged door 4 may also be provided for selective access into the internal components of the gyratory compactor apparatus 10. A display panel 80 is provided for displaying various desired parameters. Security switches may also be provided to transmit information to a control system 90 to disable motion, reset the gyratory compactor apparatus 10 to a safe position, or to shut-off power to the gyratory compactor apparatus 10. The switches may be electromechanical, electrical, or any other suitable type switch.

As generally shown in FIGS. 2 through 6, the gyratory compactor apparatus 10 generally includes a frame 12 that defines a frame axis 14 and includes a first mounting plate 16 and a spaced-apart second mounting plate 20. The frame 12 is preferably constructed using appropriate grade metal for increased structural rigidity, but is not limited to any particular material, or any particular method of construction. A pivoted support 22 is provided that is capable of rotation in at least a first and a second rotational degree of freedom, and that is carried by the first mounting plate 16.

A mold-engaging device, generally designated as 30, is provided for receiving and engaging a mold 70 that contains a material to be tested during compaction. The mold-engaging device 30 has a first carriage plate 32 positioned proximal the pivoted support 22 and a second carriage plate 34 spaced-apart therefrom to form a carriage plate assembly. Collectively, the first carriage plate 32 and the second carriage plate 34 define a space therebetween to receive the mold 70. The first carriage plate 32 is moveable in response to movement of the pivoted support 22, and likewise, movement of the pivoted support 22 imparts movement of the second carriage plate 34. The carriage plates 32 and 34 are shown throughout the figures in a flat, saucer pan-like configuration, but are not so limited by the claims and may take any appropriate shape.

Figure 2:
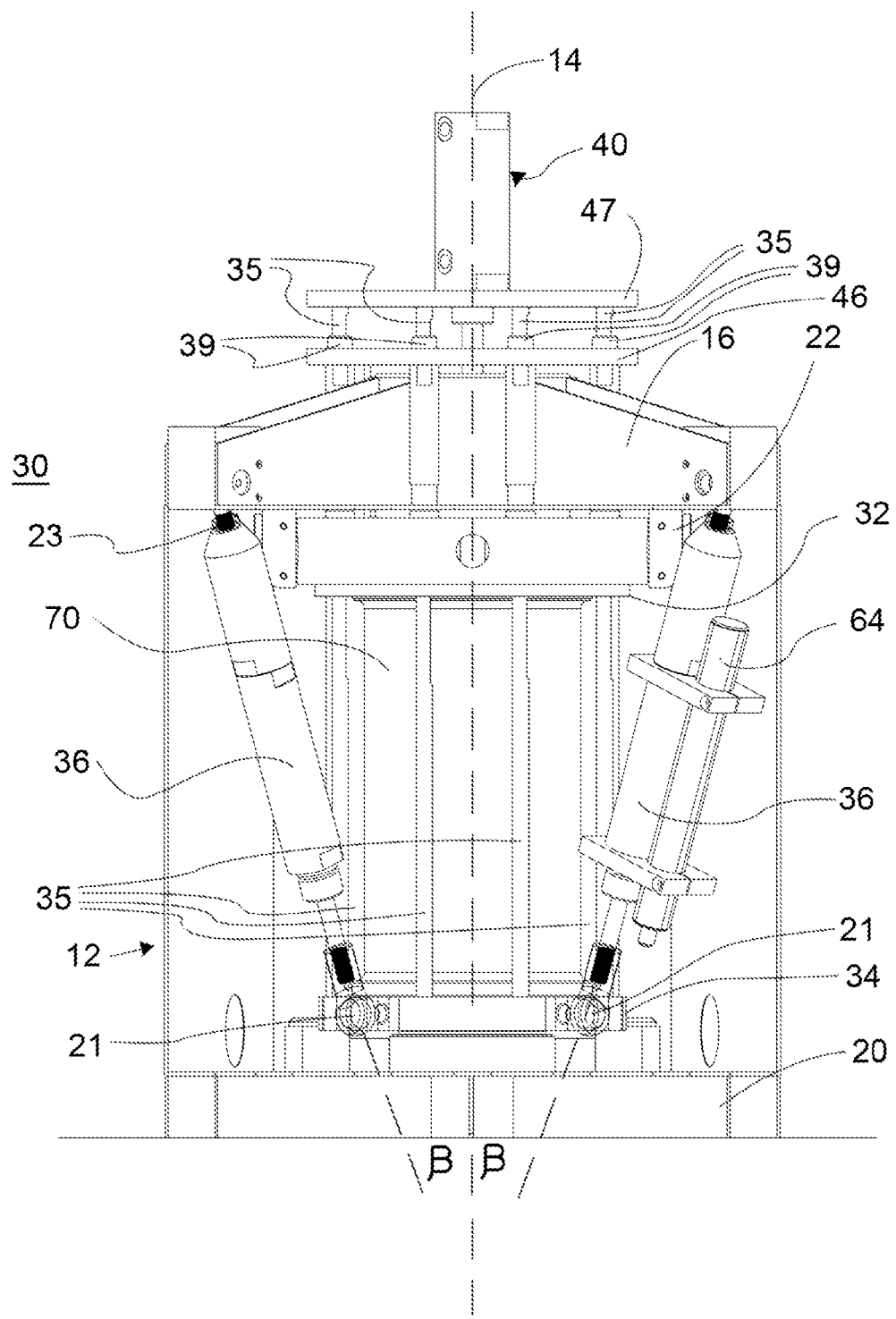
FIG. 2 is an enlarged, front view of a gyratory compactor apparatus according to an embodiment of the presently disclosed subject matter.

As shown in FIG. 2, at least one actuator 36 is provided for generating a gyratory offset of the mold 70 during compaction. The actuator 36 includes a first end carried by the frame 12 and a second end carried by the second carriage plate 34 that allows motion along at least two degrees of freedom. The actuator 36 imparts lateral movement to the second carriage plate 34 relative to the frame axis 14 to thereby define a gyratory internal angle α between the frame axis 14 and the mold axis 72, as shown in further detail in regards to the description accompanying FIG. 7. A second actuator, also designated 36, is provided. In some embodiments, it may be preferable to use only one actuator 36, or in other embodiments, it may be desirable to include multiple actuators 36. For purposes of description only, the gyratory compactor apparatus 10 is shown with two actuators 36, but the claimed subject matter is not limited to any such number of actuators 36. Each actuator 36 may include a sensor 64 that measures linear displacement, forces applied on the actuator 36, or various other desired parameters. Each actuator 36 shown in the examples of the figures is a hydraulic actuator, but in the alternative, the actuators may be an electric, pneumatic, electro-mechanical, piezoelectric, magnetorestrictive or any suitable combination thereof. The lengths, forces, and pressures associated with each actuator 36 can be independently set, measured, controlled, displayed, recorded, and transmitted.

Each actuator 36 may also include at least one pressure fitting 65 (shown in FIG. 1, but omitted from subsequent Figures for clarity purposes). The pressure fittings 65 are attached to a conventional pressure hose 67 communication with respective pressure sensors in communication with the control system 90. The actuators 36 can be positioned at an angle $\beta$ relative to the frame axis 14. The angle $\beta$ can be selected based on the size and stiffness of frame 12, as well as various other monitored parameters. In the embodiments shown throughout the figures, angle $\beta$ is about 23 degrees; however, the presently disclosed subject matter is not limited to any such angle. In other configurations of the gyratory compactor apparatus 10 may utilize carriage plates 32, 34 with geometries that are not limited to a flat surface and can include any kind of three dimensional shape. Angle $\beta$ can then be suitably optimized for each given configuration. As will be described in more detail herein, the sensors 64 may be in communication with an appropriately programmed processor of control system 90 for monitoring and controlling various desired data parameters. Transducers measure the pressure of hydraulic fluid about pressure fittings 65. However, other types of pressure transducers can be used such as load cells, a calibrated extensometer, electrical power measurement, or other suitable instruments. In instrumented gyratory compactor apparatus, at least one of the actuators including but not limited to lateral motion actuators 36, ram rod 54, and translation mechanism 40 have their position and associate force can be measured, recorded, controlled, stored, displayed, transmitted, and analyzed, in real-time or at predetermined positions, or predetermined times. The related measurement or information may be displayed, stored, transmitted, and analyzed inside the gyratory compactor apparatus 10 via the control system 90. This information can also be transmitted with a wire or wirelessly to an external computation unit for analysis, storage, printing, display. These measurements can then in turn be used to control the actuator 36 location and/or exerted force. In some embodiments, the gyratory compactor apparatus 10 may not include load sensors. However, the configuration may be upgraded to include some or all pressure sensors.

Figure 3:
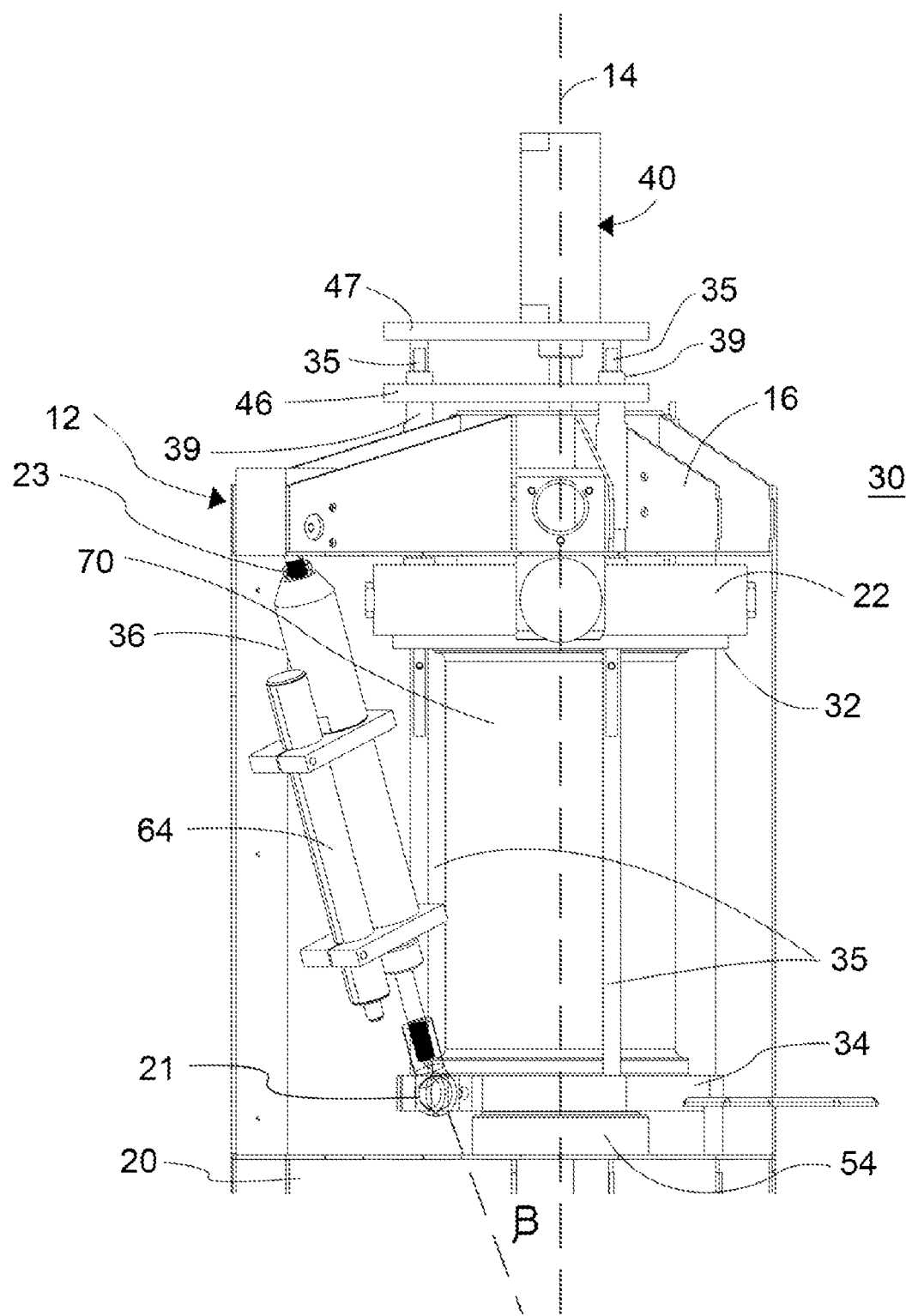
FIG. 3 is an enlarged, side view of a gyratory compactor apparatus according to an embodiment of the presently disclosed subject matter.

As shown in greater detail in FIG. 3, each actuator 36 attaches to the second carriage plate 34 and enables motion in at least two degrees of freedom. In the embodiment shown in FIG. 3, a slot 19 is formed in a flange extending from the second carriage plate 34. The slot 19 houses a swiveling joint 21, which may be a conventional heim joint type design. A corresponding slot 17 is also formed in the first mounting plate 16 for attaching to the other end of each actuator 36, which also houses a swiveling joint 23. The corresponding swiveling joint can be configured to minimize backlash, to prevent non linear behavior in position during motion and under different forces, loads and/or moments. A plurality of clamping rods 35 span between the first carriage plate 32 and the second carriage plate 34 for providing additional support to the mold engaging device 30 and for providing slideable translation of the second carriage plate 34 about the frame axis 14.

Figure 4:
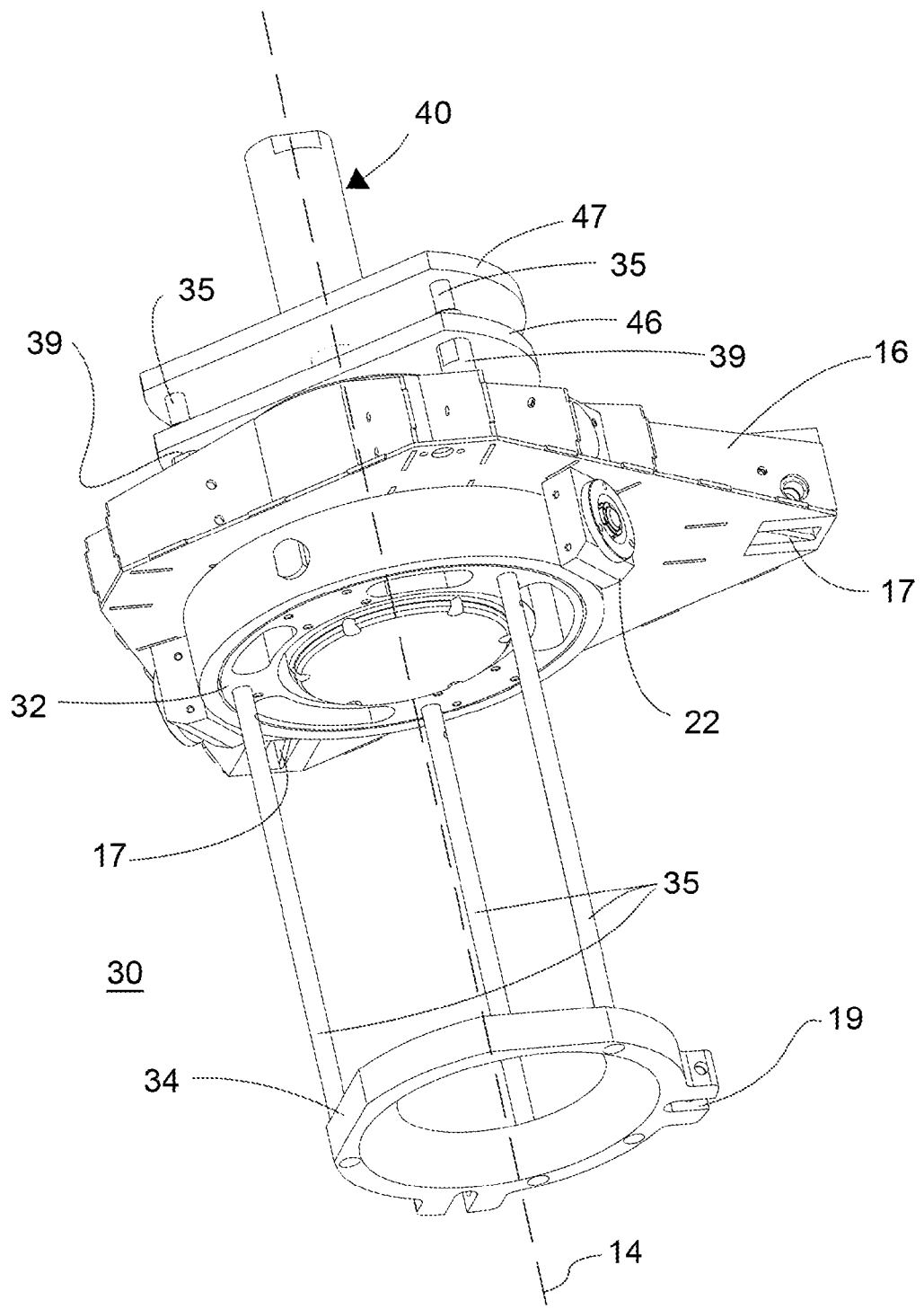
FIG. 4 is an upward facing perspective view of a mold engaging device for use with the gyratory compactor apparatus.
Figure 5:
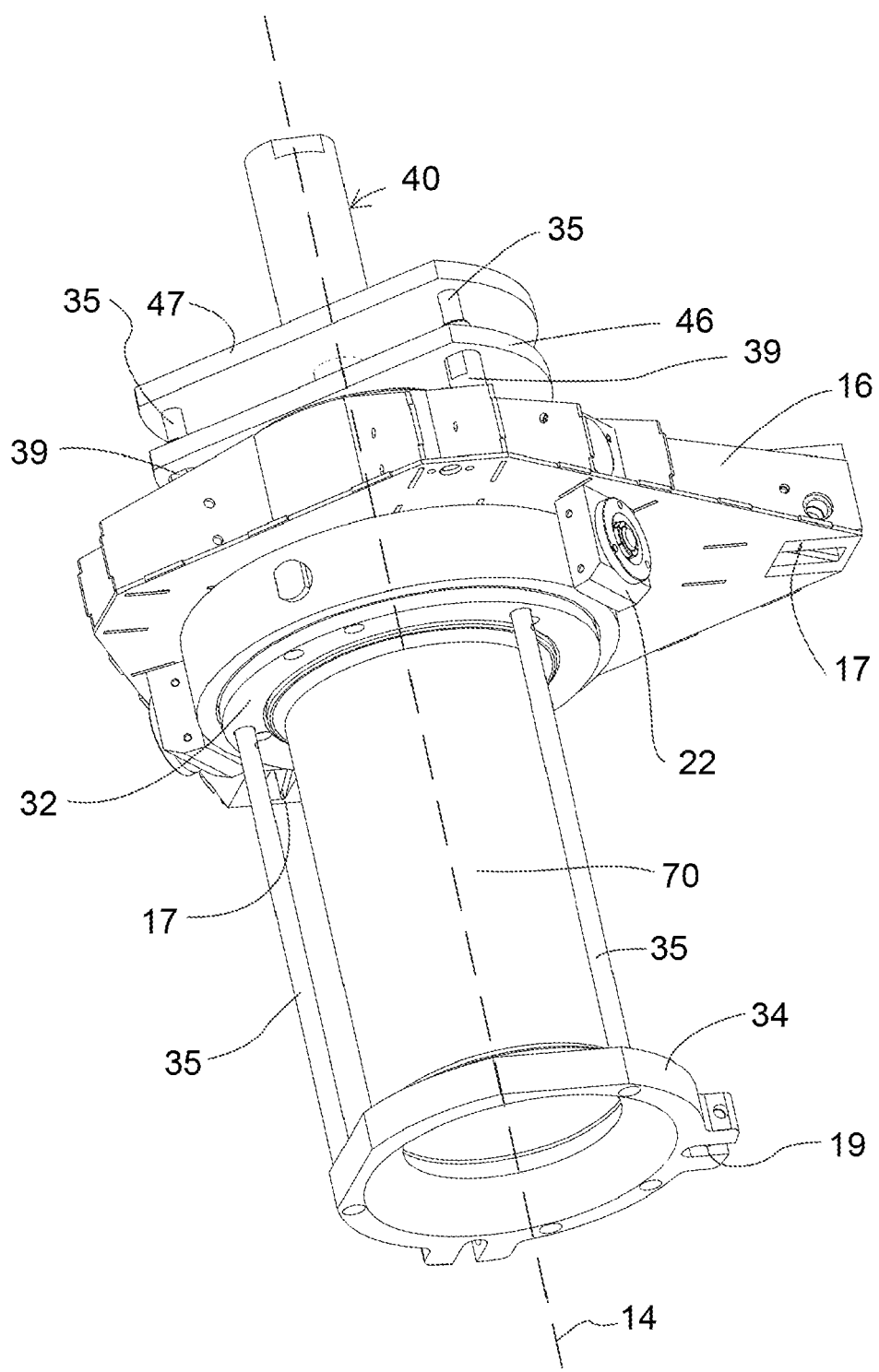
FIG. 5 is an upward facing perspective view of the mold engaging device shown in FIG. 4 having a mold engaged therewith for receiving a construction sample.

The mold-engaging device 30 is shown in greater detail in FIGS. 4 and 5. As shown in FIG. 5, the mold-engaging device 30 includes the first carriage plate 32 and the spaced-apart second carriage plate 34. The plurality of clamping rods 35 extend between a periphery of the first carriage plate 32 and of periphery of the second carriage plate 34. The mold-engaging device 30 is shown without engagement with the mold 70 in FIG. 4 and in engagement with the mold 70 in FIG. 5. Engagement of the mold 70 is effectuated by actuating the translation mechanism 40, which then that imparts translation to the first carriage plate 32 about the frame axis 14 until the first carriage plate 32 contacts the mold 70 and additionally provides clamping forces to the mold 70. As the mold-engaging device 30 relies primarily on the ends of the mold 70 for clamping purposes, the mold shape, height, and diameter is not restricted and various other mold designs may be employed. Also, the majority of clamping forces are imparted to the first mounting plate 16 such that flexure of the frame and other components of the gyratory compactor apparatus 10 is reduced or better controlled.

Figure 6:
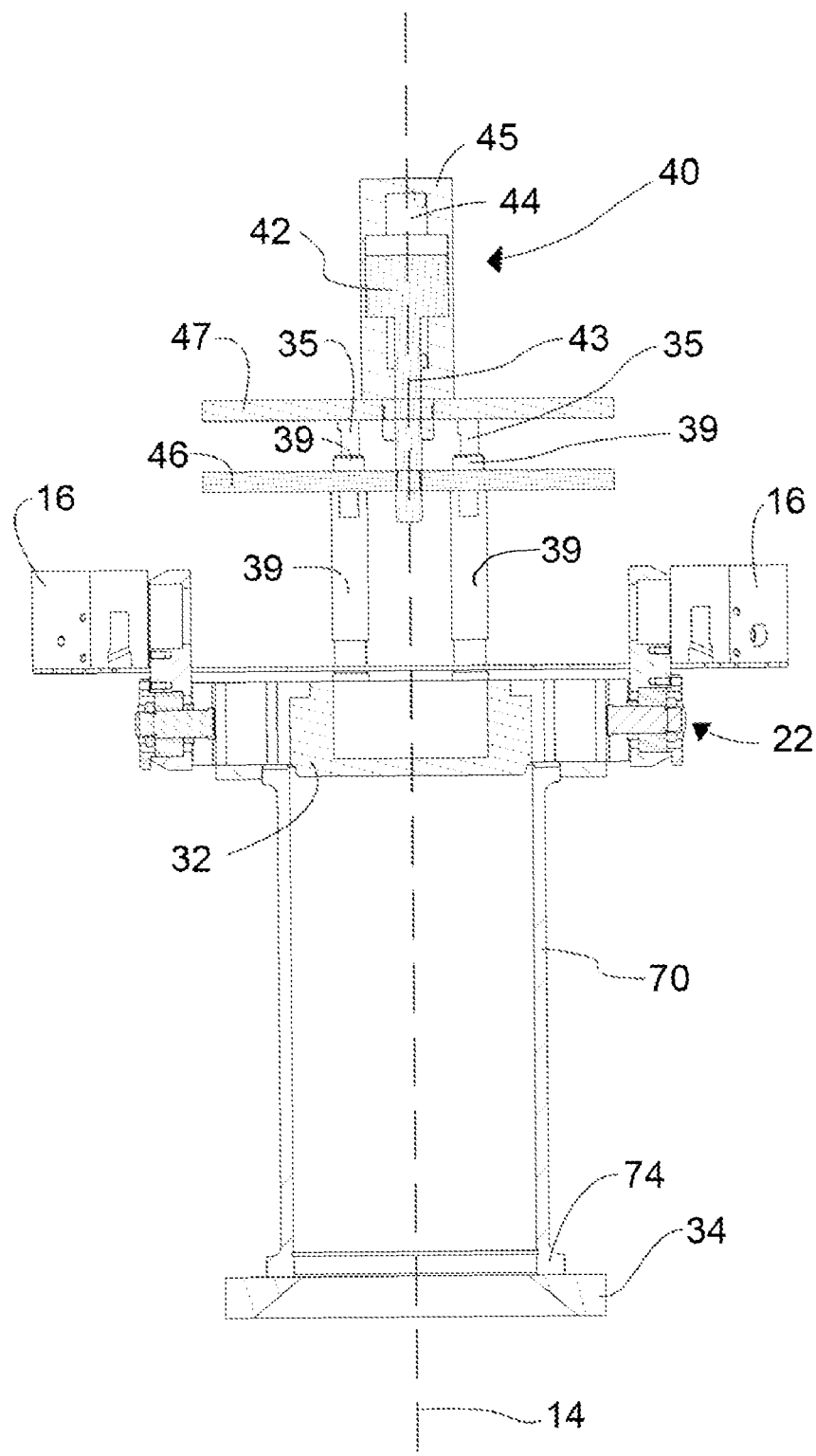
FIG. 6 is a cross-sectional view of a mold engaging device of the gyratory compactor apparatus according to an embodiment of the presently disclosed subject matter.

A cross-sectional view of the mold-engaging device 30 and pivoted support 22 is shown in FIG. 6. In some embodiments, the pivoted support 22 is a gimbal of the type known in the art, but in appropriate circumstances could be a spherical bearing or any other joint or structure capable of rotation within an appropriate range of directions. A first clamping plate 46 and a second clamping plate 47 collectively form a pair of clamping plates. A plurality of sleeves 39 are carried by the first clamping plate 46. The sleeves 39 are configured for slideably receiving a respective clamping rod 35 within. The translation mechanism 40 functions by having a piston 42 slideably positioned within a cylinder 44 that is defined within a housing 45. The piston 44 is in contact with the first clamping plate 46 by rod 43 such that an increase in pressure within the piston cylinder 44 imparts downward forces onto the first clamping plate 46 and causes upward translation of the second clamping plate 47. This is turn causes translation of clamping rods 35 away from the mold and thus imparts translation of the second carriage plate 34 until the second carriage plate 34 comes into mating engagement with the mold 74, thereby securing the mold 70 in place between the first carriage plate 32 and the second carriage plate 34. While the translation mechanism 40 is shown in the figures as a hydraulic actuator, the presently claimed subject matter is not limited to any specific design and could utilize electromechanical, mechanical, pneumatic, or other suitable designs, or combinations thereof.

In alternate embodiments, an alternate translation mechanism can engage the second carriage plate 34 and impart compression forces via at least one pneumatic, hydraulic, piezoelectric, or magneto restrictive actuators or any combination thereof.

Figure 7A:
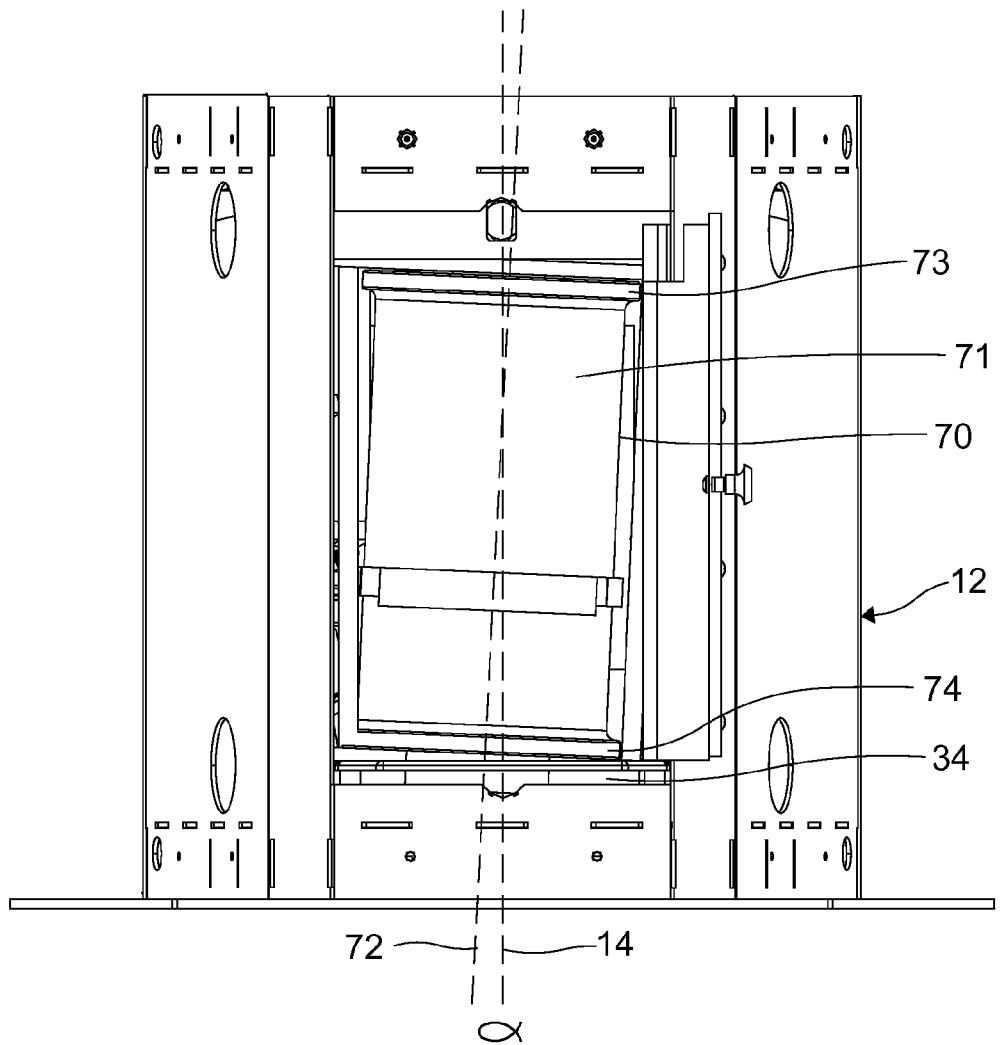
FIG. 7A is a side view of the mold showing the gyratory internal angle defined between the frame axis and the mold axis during gyration of the mold according to an embodiment of the presently disclosed subject matter.
Figure 7B:
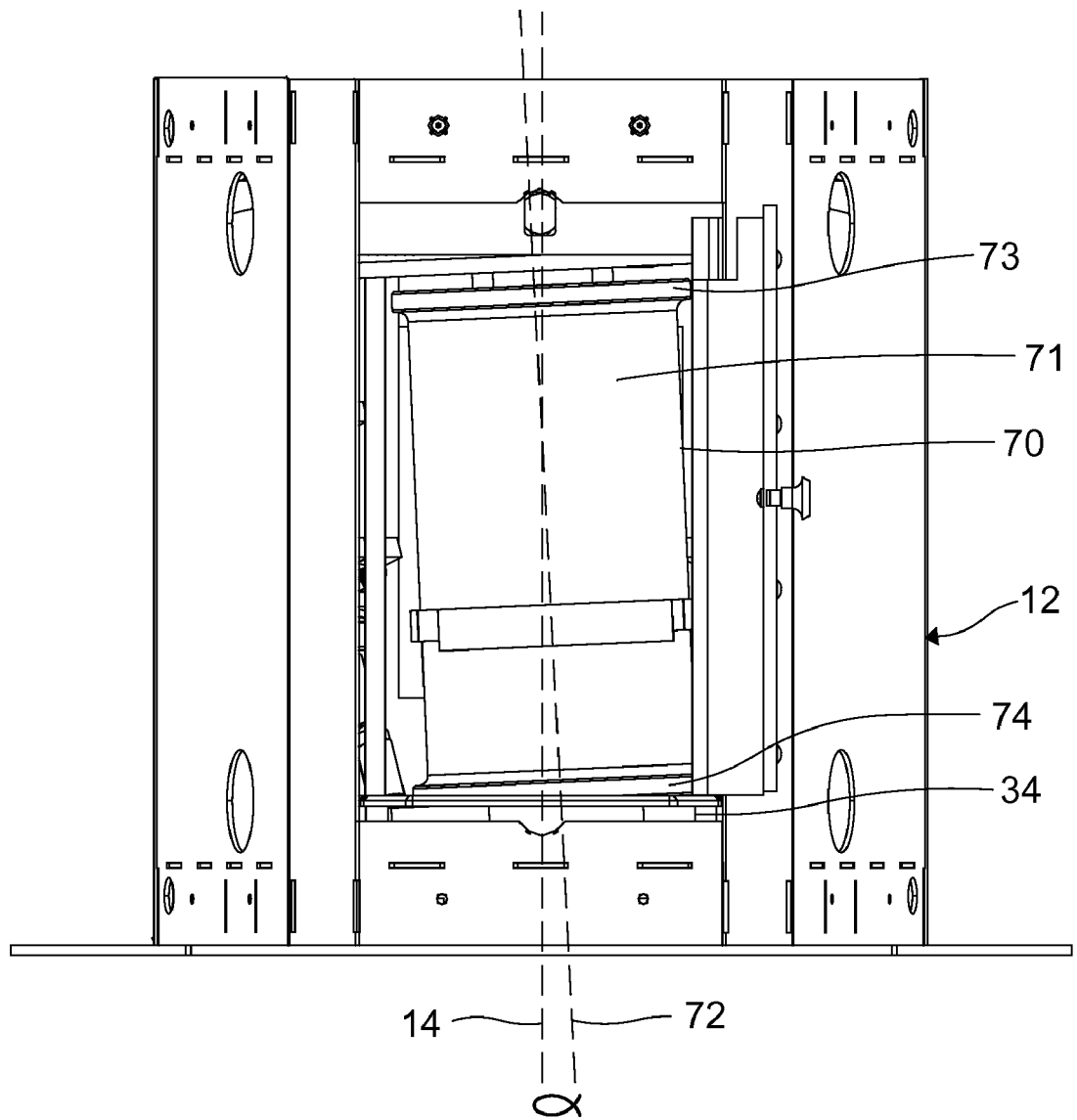
FIG. 7B a side view of the mold shown in FIG. 7A where the mold has been rotated half of a rotation about the frame axis.

An internal angle $\alpha$ is defined between a mold axis 72 formed about a central vertical of the mold 70 and the frame axis 14 as shown in FIG. 7A and FIG. 7B. Moreover, the gyratory orbit generated by the actuator 36 can be controlled so that the internal angle $\alpha$ is consistent as a function of time in order to take into account the variability of the frame 12 flexure, relative changes in the position between the first carriage plate 32 and second carriage plate 34, and the position of the ram rod 54. FIG. 7A details the gyratory compactor apparatus 10 gyrating the mold 70 towards a first direction, while FIG. 7B shows the gyratory compactor apparatus 10 gyrating the mold one half of a rotation beyond that which is shown in FIG. 7A. The internal angle $\alpha$ measured may be measured instantaneously, time-delayed, or averaged over a predetermined period of time.

Figure 8:
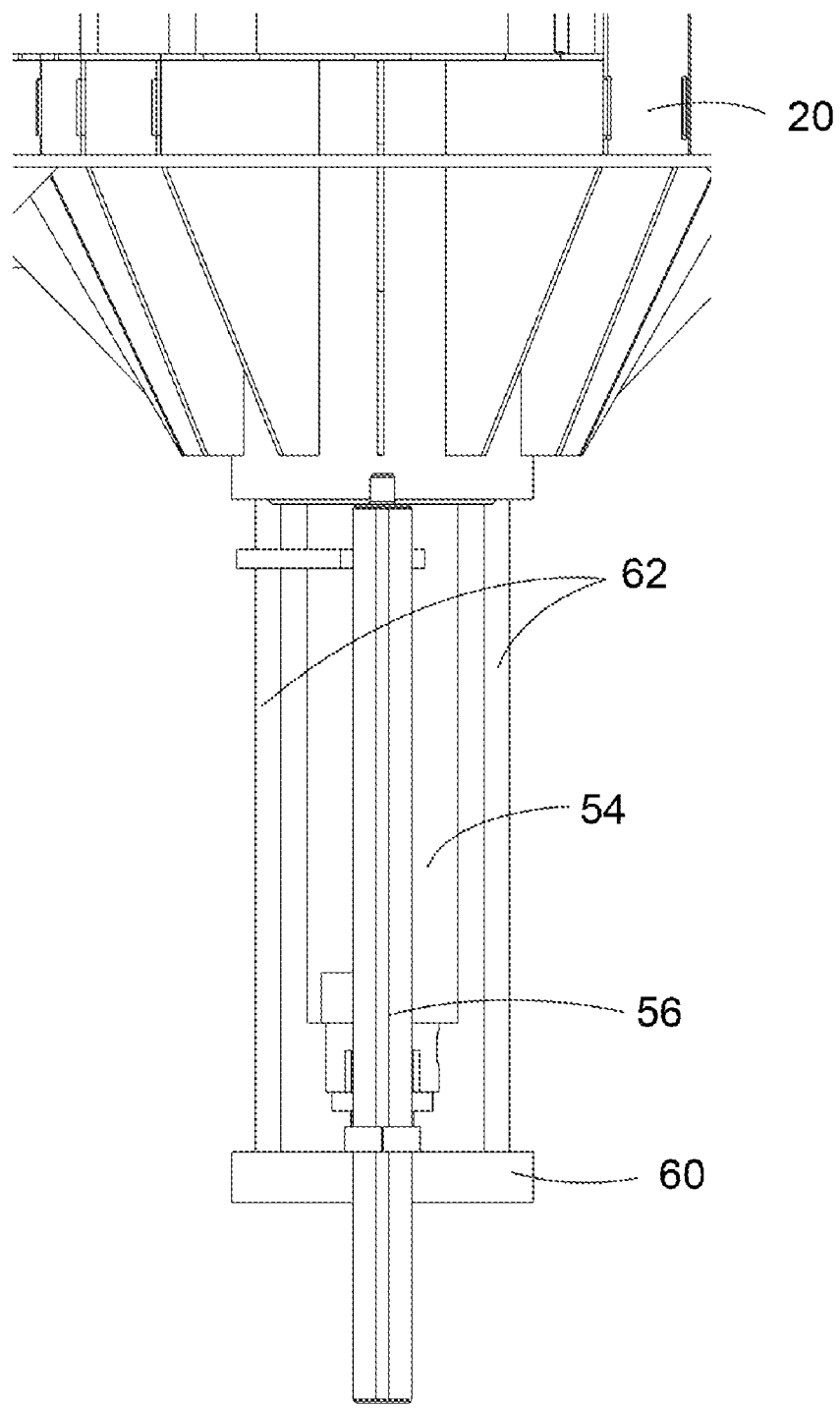
FIG. 8 is a front view of a ram rod and anti-rotation plate for use with the gyrator compactor apparatus according to an embodiment of the presently disclosed subject matter.
Figure 9:
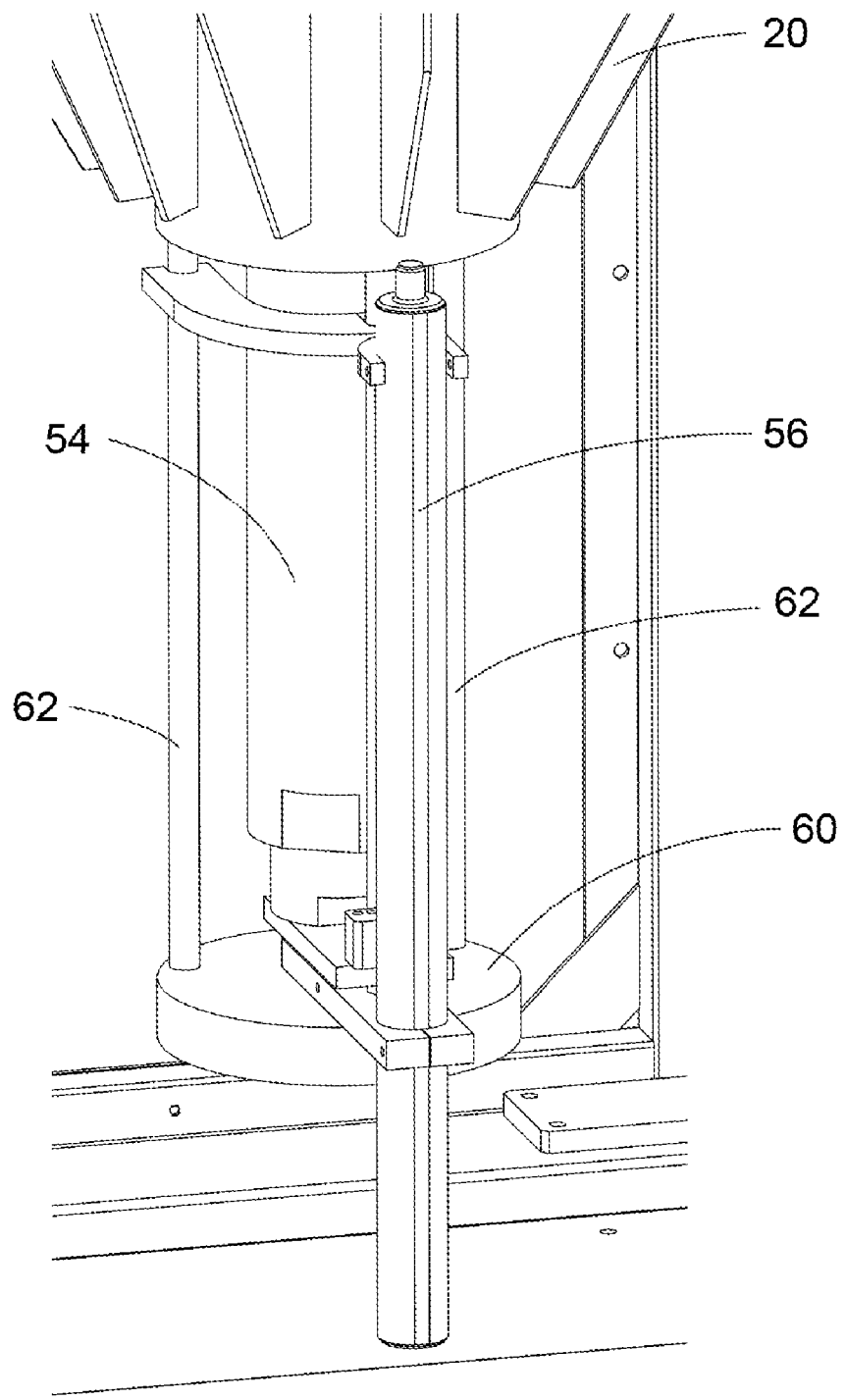
FIG. 9 is a downward facing, perspective view of the ram rod and anti-rotation plate shown in FIG. 8 for use with the gyratory compactor apparatus according to an embodiment of the presently disclosed subject matter.

As shown in FIGS. 8 and 9, the ram rod 54 is provided proximal the second mounting plate 50. The ram rod 54 acts to provide compressive forces to the mold 70 about the frame axis 14. A linear displacement device 56 may be provided for measuring displacement relative to the ram rod 54. An anti-rotate plate 60 is positioned on a distal end of the ram rod 54 for torsional rigidity to retard rotating forces from rotation of the ram rod 54. The anti-rotate plate 60 includes a plurality of spaced-apart support beams 62 that are each carried on a first end about a periphery of the anti-rotate plate 60 and that are each carried on a second end at the second mounting plate 20. These beams 62 act to retard rotating forces from rotation of the ram rod and thus provide a more accurate and controlled testing environment.

Figure 10:
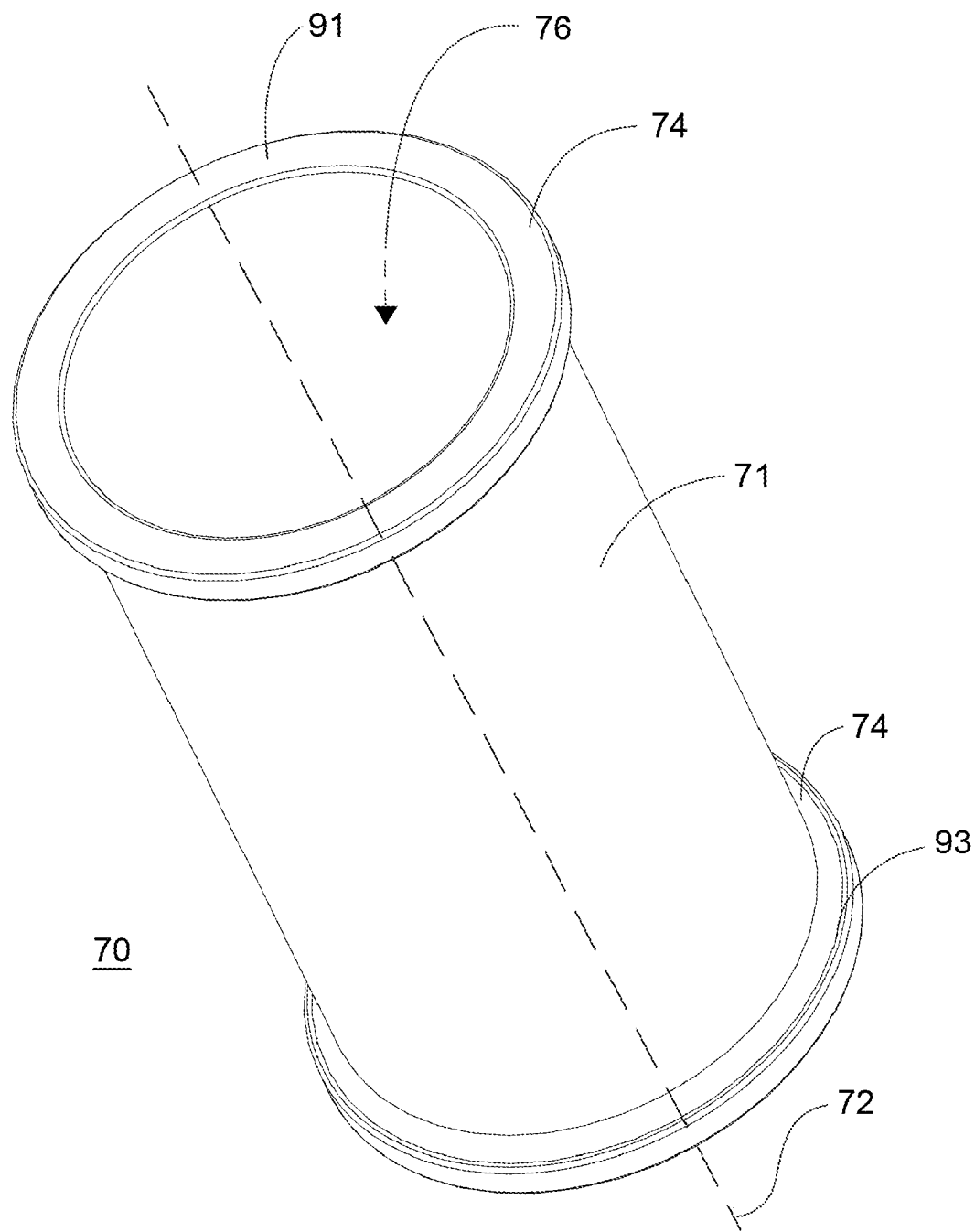
FIG. 10 is a perspective view of a mold of the type for being used with the gyrator compactor apparatus according to an embodiment of the presently disclosed subject matter.
Figure 11:
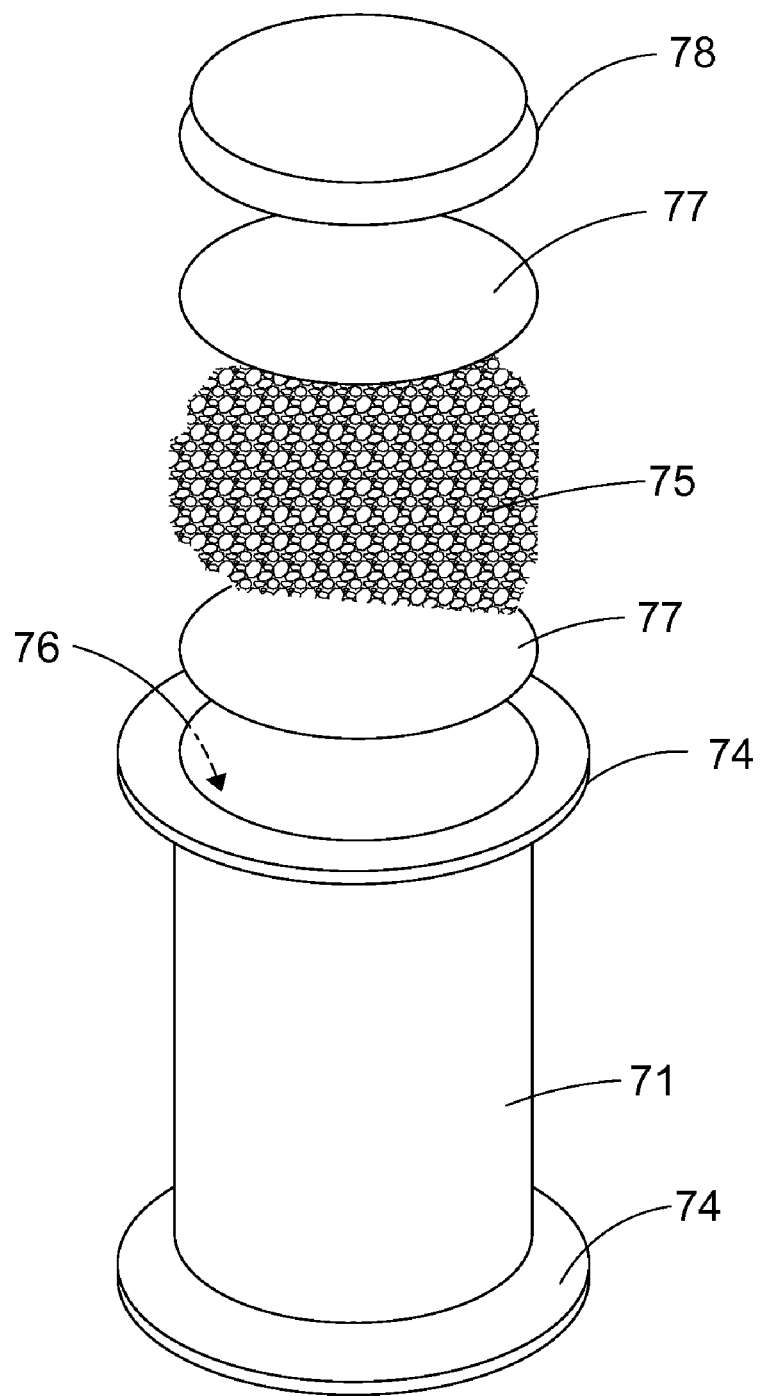
FIG. 11 is a perspective view of the mold shown in FIG. 9 having a sample of material shown in an exploded view for being deposited therein.

A mold 70 of the type for use with the gyratory compactor apparatus 10 is shown in FIG. 10 and FIG. 11. The mold 70 includes a cylinder 71, a first peripherally extending flange 73 at a first end 91 and second peripherally extending flange 74 at a second opposing end 93 of the cylinder 71. The mold 70 is adapted for receiving a volume of material to be compacted within a void, generally designated 76, defined within the cylinder 71. The mold 70 is typical of the type of mold routinely employed within relevant compactor industries, however, the presently claimed subject matter is not limited to any particular shape of mold.

Figure 13:
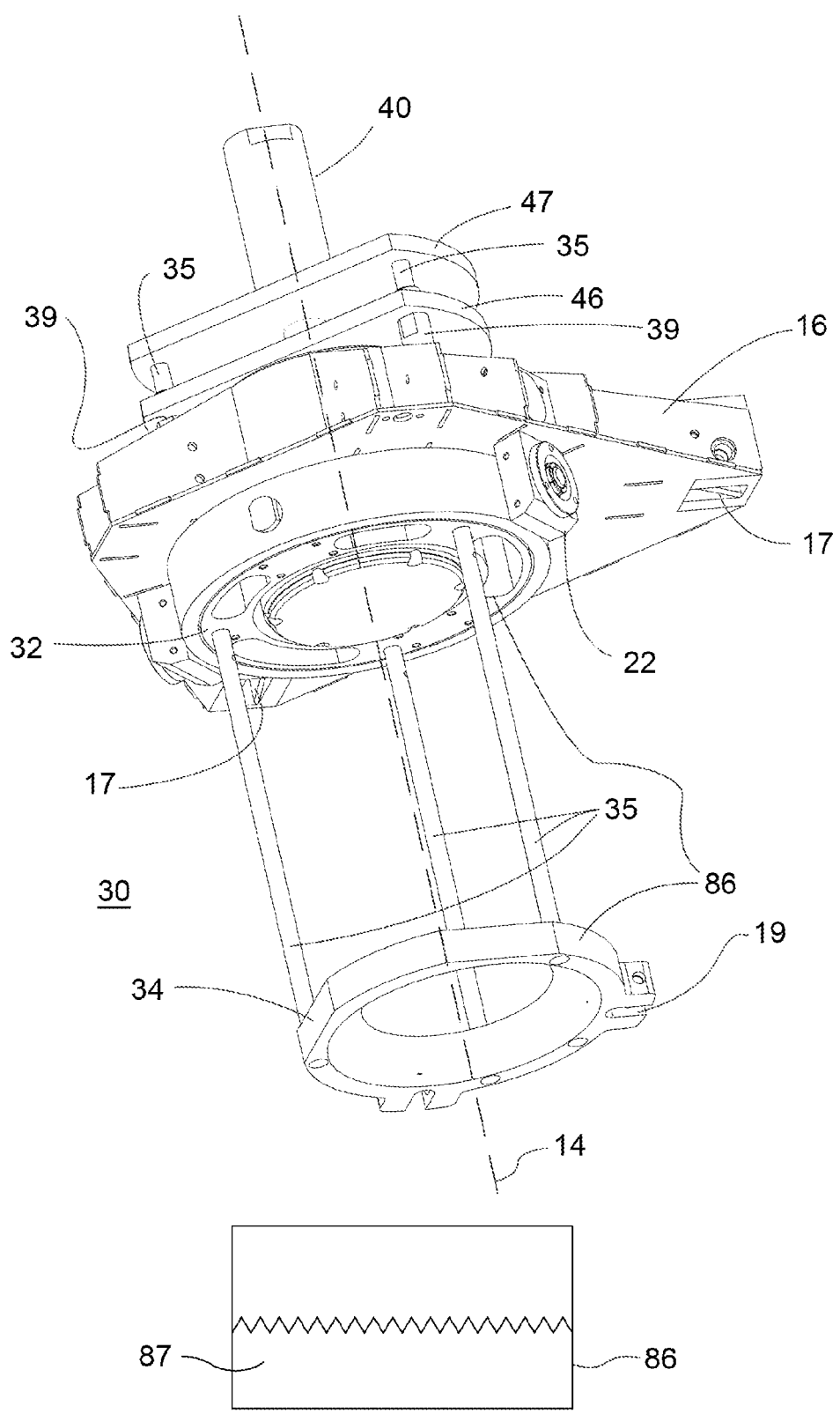
FIG. 13 is an upward facing perspective view of a mold engaging device having an engagement surface with a textural feature defined thereon.
Figure 14:
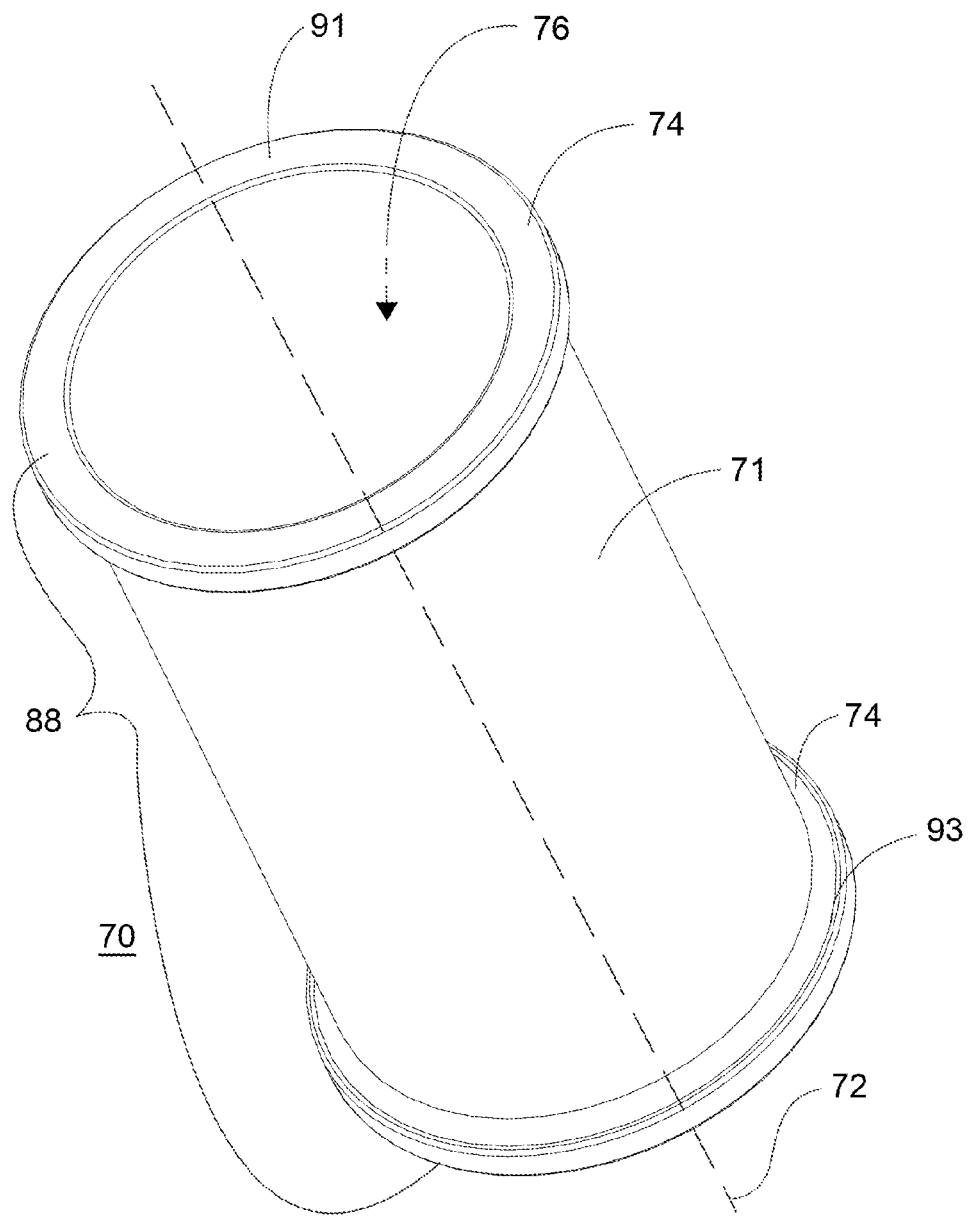
FIG. 14 is a perspective view of a mold of the type for being used with the gyratory compactor apparatus and having a textural feature defined on at least one end of the mold.

As shown in FIG. 13, at least one of the carriage plates 32, 34 may define textural features 86 that are configured to increase axial friction to aid with clamping of the mold and to reduce the axial forces that must be generated to maintain the mold 70 within the mold-engaging device 30. The textural features 86 may be grooves, such as are shown as 87 in FIG. 13, etching, carving, chiseling, sandblasting, or any other suitable feature, or the features may be added by the addition of at least one layer containing anti slippage or friction increasing properties. Similarly, as shown in FIG. 14, at least one of surfaces 91 or 93 of the mold 70 may also possess textural features 88 or at least one. A representative embodiment showing grooves 89 is presented in FIG. 14, but any suitable textural feature 88 may be employed. In this regard, flanges 73 and 74 may not be necessary to use with the gyratory compactor apparatus 10, as the textural features 86, 99 may be all that is required to hold the mold 70 between the first carriage plate 32 and the second carriage plate 34.

Operation of the gyratory compactor apparatus and preparation of the testing specimen will now be described. A suitable sample of material to be compacted is first prepared by mixing appropriate aggregates. Typically, the gyratory compactor apparatus will be used for mixing asphalt. When mixing asphalt, the asphalt composition is heated to a predetermined temperature along with the mold 70. The mold 70 and asphalt are not typically heated above 350 degrees Fahrenheit, but in appropriate circumstances may be heated to any suitable temperature depending on the material to be tested.

As shown in FIG. 11, a first puck (not shown) can be inserted into the cavity 76 of the mold, and then a first piece of specimen paper 77 is placed on the first puck within the cavity 76 of the mold 70. The heated asphalt mixture 75 or soil mixture specimen is then placed within the mold 70. A second piece of specimen paper 77 is placed above specimen 75 before finally placing a second puck 78 within the cavity 76 of the mold 70. Both the first puck and the second puck 78 are typically heated with the mold 70 and specimen 75 to ensure proper heat expansion and contraction, as well as to maintain a consistent environmental testing standard.

The mold 70 is then inserted between the first carriage plate 32 and the second carriage plate 34. The translation mechanism 40 is then actuated to impart translation of the second carriage plate 34 until the mold 70 is firmly held between the first carriage plate 32 and the second carriage plate 34 as described in the description accompanying FIGS. 4, 5, and 6. Once the mold 70 is correctly positioned and engaged within the mold-engaging device 30, the operator selects a set of predetermined parameters such as gyratory internal angle α, the pressure of the ram rod 54, the displacement of the ram rod 54, and the number of gyrations, among other parameters. Gyration and compaction continue until a desired parameter is met, such as displacement of the ram rod 54 or number of gyrations.

In appropriate circumstances, the gyratory compactor apparatus 10 monitors the compaction pressure of the ram rod 54, and if compaction pressures of the ram rod fall within or out of a desired, predetermined range of pressures, the gyratory compactor apparatus 10 may be designed to cease operation at that time.

Once the desired amount of compaction of the specimen 75 is achieved, the compacted specimen is removed from the mold 70. Appropriate testing such as determining density and other desired test parameters are then carried out on the compacted specimen.

Figure 12:
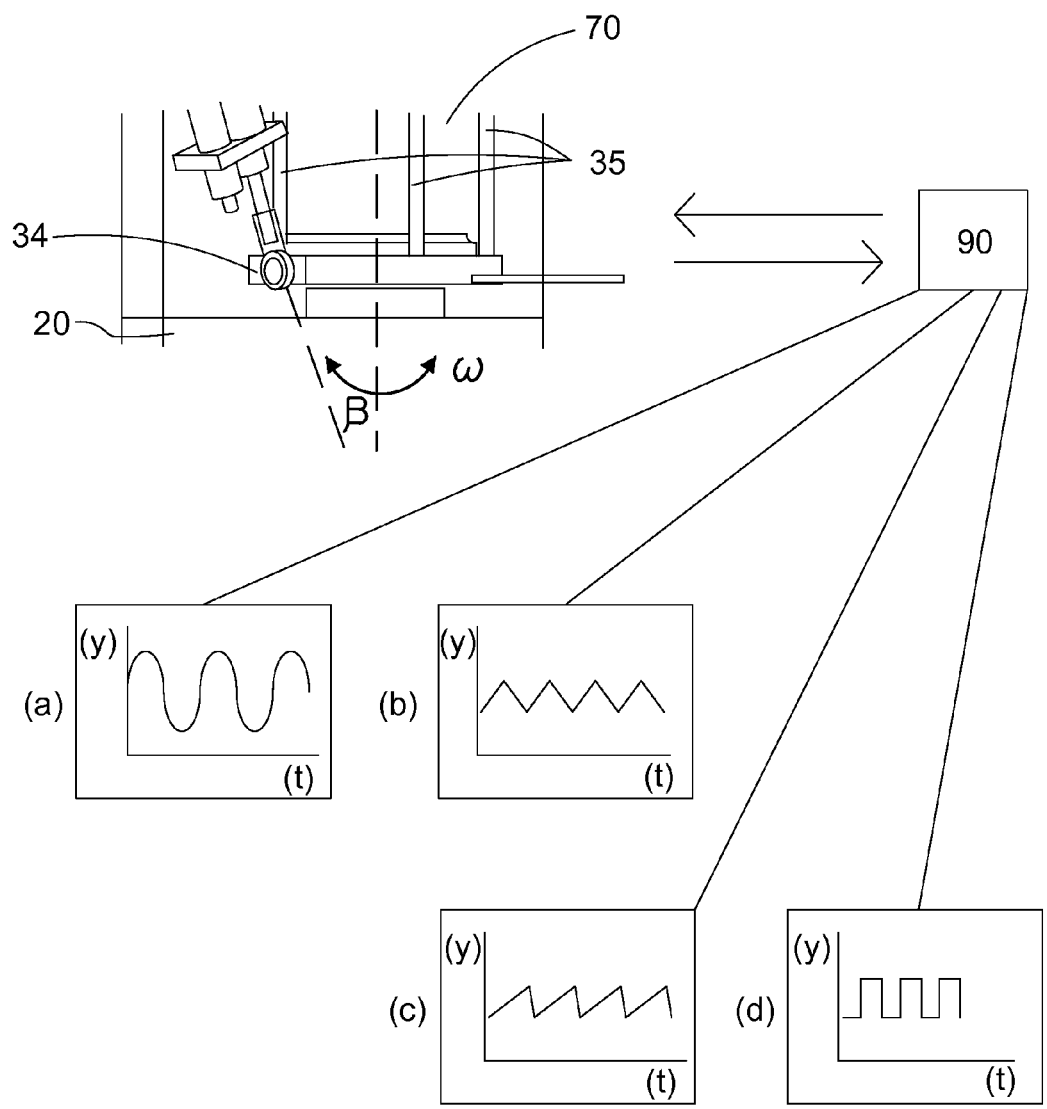
FIG. 12 is an enlarged, side view of the gyratory compactor apparatus in communication with a control system for outputting predetermined wavefunctions for controlling vertical translation of the ram rod.

The ram rod 54 is configured such that the operator of the gyratory compactor apparatus 10 can select the compressive characteristics of the ram rod 54. As shown in FIG. 12, the ram rod 54 applies vertical compressive forces to the mold 70 and is configured to travel in a vertical, longitudinal direction as represented by an upwards arrow and "y." The ram rod 54 is also configured for rotational movement about the frame axis 14 as represented by "ω." The ram rod 54 outputs these compressive forces by communicating with the control system 90. The control system may have a wave or signal generator in communication therewith. In some embodiments such as is shown in FIG. 12, the ram rod 54 may have a compressive function that approximates a wavefunction including but not limited to a sinusoidal, as shown in graph (a) in FIG. 12, triangular, as shown in graph (b) in FIG. 12, saw-tooth, as shown in graph (c) in FIG. 12, square, as shown in graph (d) in FIG. 12, or other desired waveforms, and in other embodiments, may also be configured to approximate other parameters associated with such waveform, including but not limited to the amplitude, phase, offset, dynamic range, time delay, and other various parameters. In each of the graphs shown in FIG. 12, the vertical axis represents vertical displacement (y) of the ram rod 54 as a function of time (t).

The control system 90 and the various techniques described herein may be implemented with hardware or software or, where appropriate, with a combination of both. The control system 90 may be a circuit board appropriately configured and mounted to apparatus 10. Further, the control system 90 may be separated from apparatus 10 in the form of a machine such as a computer in communication with components on the apparatus. Thus, the gyratory compactor apparatuses and associated methods of the disclosed embodiments, or certain aspects or portions thereof, may be controlled by the control system 90, alone or together with various other components, executing program code (i.e., instructions) embodied in tangible media, such as floppy diskettes, CD-ROMs, hard drives, or any other machine-readable storage medium. For example, the program code can be loaded into and executed by a machine, such as a computer, and the machine becomes an apparatus for practicing embodiments of the presently disclosed subject matter. In the case of program code execution on programmable computers, the computer will generally include a processor, a storage medium readable by the processor (including volatile and non-volatile memory and/or storage elements), at least one input device and at least one output device. One or more programs are preferably implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed subject matter. When implemented on a general-purpose processor, the program code combines with the processor to provide a unique apparatus that operates to perform the processing of the presently disclosed subject matter.

An important aspect to operation of gyratory compactor apparatuses as presently disclosed is calibration of various aspects of the orbital motion, internal angle, loads, mechanical moments exerted inside the mold onto the sample between the applied motion imparted and measured on or by the actuators or carriage plate assemblies and the loads, pressure, forces, moments applied on or by actuators and carriage plate assemblies, and the like. In an embodiment of the presently disclosed subject matter, a gyratory angle, either internal or external angle, can be measured at a high sampling rate. For example, a suitably configured device, such as a RAM or DAV, can measure the angle of gyration, or gyratory angle, at a high sampling rate. The measured internal angle can be used for determining adjustments to actuation of the actuators of a gyratory compactor apparatus as disclosed herein to impart to the mold a target orbit.

Due to the non isotropic flexure of various components of the overall assembly of a gyratory compactor apparatus, the motion perceived by the sample inside the mold can be significantly different from a target orbit for the mold. Apparatuses disclosed herein can use algorithms to convert the difference between the actual orbital motion of the mold and the target orbital motion for the mold into a corrected motion of the actuators to ensure proper motion. For example, one typical error is due to the slight misalignment of the actuators with respect to each other, the correction can then lead to a slight change in the time delay, also referred to as phase delay, between the actuators' motion. When the frame and/or ram of an apparatus exhibit significant difference in flexure in one or more directions, the shape of the waveform applied to the actuators control can be applied to correct for the resulting error of orbit. The type, value, correction and calibration of the waveforms may vary as the shape, dynamic range of the orbit, the amount of compressive loads change. The correction can be applied to at least one of the actuators, ram, and clamping system. The correction and the updated external orbit and related parameters can then be stored, printed, displayed, and/or analyzed.

Figure 15:
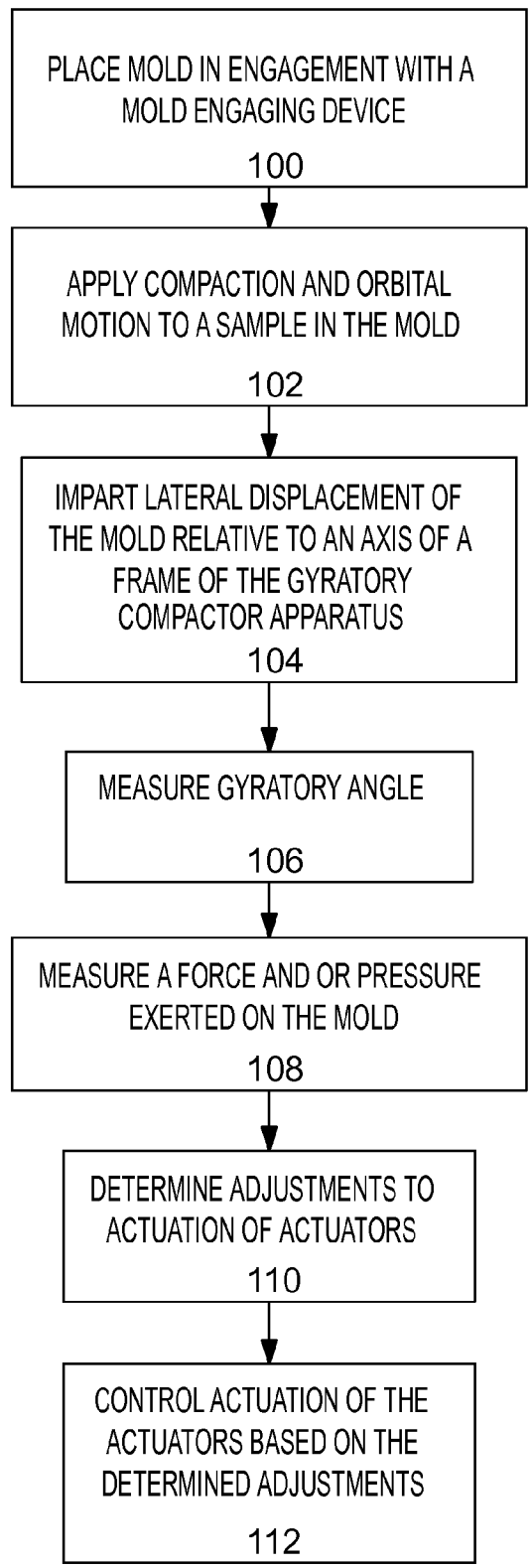
FIG. 15 is a flow chart of an exemplary process for calibrating a gyratory compactor apparatus in accordance with an embodiment of the presently disclosed subject matter.

FIG. 15 is a flow chart of an exemplary process for calibrating a gyratory compactor apparatus in accordance with an embodiment of the presently disclosed subject matter. In this example, reference is made to other embodiments of the gyratory compactor apparatus disclosed herein and shown in other figures. Referring to FIG. 15, a mold is placed in engagement with a mold-engaging device (step 100). For example, the mold 70 shown in FIGS. 7A and 7B can be placed in engagement with the mold-engaging device 30 shown in FIG. 4 in accordance with the disclosure herein. The mold can contain a sample or material to be tested during compaction.

At step 102, compaction and orbital motion are applied to a sample in the mold. For example, the ram rod 54 shown in FIG. 1 can apply rotational movement and compressive forces to the mold about the frame axis. The control system 90 can control movement of the ram rod 54.

At step 104, lateral displacement of the mold relative to an axis of a frame of the gyratory compactor apparatus is imparted by actuation of one or more actuators. As a result, a gyratory angle between the frame axis and the mold axis is defined. For example, referring to FIGS. 7A and 7B, the control system 90 can control actuation of the actuators 36 such that the internal angle α is defined between a mold axis 72 formed about a central vertical of the mold 70 and the frame axis 14. Steps 102 and 104 can occur simultaneously.

At step 106, the gyratory angle is measured. For example, the measurement of the gyratory angle, either internal or external angle, can be measured instantaneously for each rotation of the mold relative to each rotation of the mold. The measurement of the gyratory angle may also be averaged for each rotation of the mold. The measurement can be performed directly without limitation by one or more inclinometers operative to the inside or outside of the mold or an internal angle measurement device such as a RAM or DAV, or the measurement can be performed indirectly by the location of at least one of the carriage plate assemblies or the position of at least one actuator lengths. These measurements can be taken continuously or at least one predetermined position in the orbit of the motion, or at least one predetermined time of operation including at predetermined intervals of times. A typical parameter to be concerned with for calibration is the synchronization delay between the forces/position between the at least one actuators in order to generate a circular motion, without such proper synchronization the orbit perceived by the sample under test may be elliptical in shape.

At step 108, a force and/or pressure exerted on the mold can be measured. For example, the sensors 64 or various other sensors may be in communication with the control system 90 for monitoring various data parameters of the gyratory compactor apparatus. Further, for example, various types of pressure transducers can be used for measure force and/or pressure on the mold such as load cells, a calibrated extensometer, electrical power measurement, or other suitable instruments. The lateral motion actuators 36, ram rod 54, and/or translation mechanism 40 may also have their positions and associated forces measured, recorded, stored, displayed, transmitted, and analyzed, in real-time or at predetermined positions, or predetermined times.

At step 110, adjustments to actuation of one or more actuators are determined based one or a combination of the measured gyratory angle, a target angle, the measured force, and the measured pressure. For example, the control system 90 can apply an algorithm for determining adjustments to the actuators 36 based on the measured gyratory angle and a target angle. An operator of the apparatus may desire that the gyratory angle between the apparatus frame and the mold axis form a target angle in a particular testing run. To do so, the operator may program the control system 90 with the desired target angle such that the algorithm uses the programmed target angle and one or more acquired measurements to determine actuator adjustments.

At step 112, actuation of one or more of the actuators is controlled based on the determined adjustments. For example, the control system 90 can utilize adjustments calculated by the algorithm to determine inputs for the actuators 36. As a result, when the actual gyratory angle differs from the target gyratory angle, the actuators 36 can be controlled to make corrections such that the actual gyratory angle matches the target gyratory angle.

Figure 16:
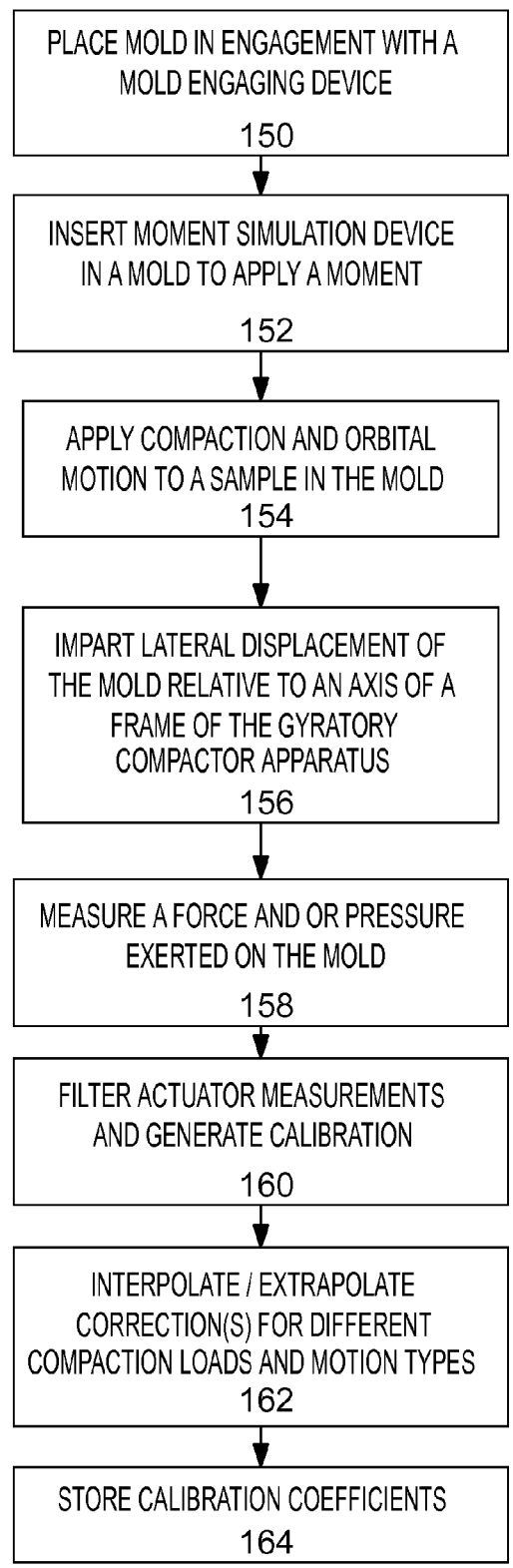
FIG. 16 is a flow chart of another exemplary process for calibrating a gyratory compactor apparatus in accordance with this embodiment of the presently disclosed subject matter.

Measurement of forces applied to a mold of a gyratory compactor apparatus and measurements of geometric changes to a frame of the apparatus may not be sufficient to estimate a complete set of forces applied to the mold. For example, a moment simulation device, such as a RAM or DAV, can be inserted into a mold and can be utilized to obtain a simulated moment measurement when compressive forces are applied to it. Such a simulation can be performed with or without orbital motion of the mold. However, the measurements may not be accurate. In accordance with an embodiment of the presently disclosed subject matter, a method is provided to calibrate the moment simulation device using such measurements by using one or more of pressure and/or force measurements on the lateral actuators (e.g., actuators 36), compressive actuators (e.g., used to move the ram rod 54), and clamping actuators applied to the gyratory compactor apparatus. The calibration can be performed under different values of angle, orbit shape, motion, and static positions. The calibration can utilize a model or algorithm that is not limited to polynomials of any order, and it may also include non-separable components of non-linear mathematical functions. Moreover, these values may be interpolated or extrapolated to values inside or outside the range of parameters that are described. Moreover, these calibration values can be estimated and set by default based on the previous geometric angle calibration. Based upon this calibration, the shear moment, shear pressure, shear force, and eccentricity can be displayed, stored, analyzed, and printed. FIG. 16 is a flow chart of an exemplary process for calibrating a gyratory compactor apparatus in accordance with this embodiment of the presently disclosed subject matter. In this example, reference is made to other embodiments of the gyratory compactor apparatus disclosed herein and shown in other figures.

Referring to FIG. 16, a mold is placed in engagement with a mold-engaging device (step 150). For example, the mold 70 shown in FIGS. 7A and 7B can be placed in engagement with the mold-engaging device 30 shown in FIG. 4 in accordance with the disclosure herein. The mold can contain a sample or material to be tested during compaction.

At step 152, a moment simulation device is inserted in the mold to apply a moment. For example, a RAM or DAV can be inserted in the mold 70 for applying a moment.

At step 154, compaction and orbital motion are applied to a sample in the mold. For example, the ram rod 54 shown in FIG. 1 can apply a lateral displacement and compressive forces to the mold about the frame axis. The control system 90 can control movement of the ram rod 54. The lateral displacement may be static or dynamic orbital motion.

At step 156, lateral displacement of the mold relative to an axis of a frame of the gyratory compactor apparatus is imparted by actuation of one or more actuators. As a result, a gyratory angle between the frame axis and the mold axis is defined. For example, referring to FIGS. 7A and 7B, the control system 90 can control actuation of the actuators 36 such that the internal angle α is defined between a mold axis 72 formed about a central vertical of the mold 70 and the frame axis 14. Steps 154 and 156 can occur simultaneously.

At step 158, actuator loads, pressures, and moments exerted on the mold are measured. For example, the sensors 64 or various other sensors may be in communication with the control system 90 for monitoring various data parameters of the gyratory compactor apparatus. Further, for example, various types of pressure transducers can be used for measure force and/or pressure on the mold such as load cells, a calibrated extensometer, electrical power measurement, or other suitable instruments. The lateral motion actuators 36, ram rod 54, and/or translation mechanism 40 may also have their positions and associated forces measured, recorded, stored, displayed, transmitted, and analyzed, in real-time or at predetermined positions, or predetermined times.

At step 160, actuator measurements are filtered, and calibration generated. The calibration can be generated to convert these measurements into moment exerted into sample based on selected calibration function. For example, the control system 90 can determine a relationship between the measured force applied by one or more of the actuators 36 and the applied moment.

At step 162, one or more corrections for different compaction loads and motion types can be one or both of interpolated and extrapolated. The interpolation functions may be polynomial with or without separable components, logarithmic, exponentional or any combinations of linear or non-linear mathematical functions. At step 164, one or more calibration coefficients can be stored.

According to one embodiment, the gyratory compactor apparatus can include a display configured to display one of error of the measurement of the actual moment from a target moment, a three-dimensional representation of the actual moment, shear pressure, shear moment, eccentricity, eccentricity vector, or any other information related to moments, information relative to the passing/failing of criteria of target moment information, and average values or information relative to moment. The control system 90 can communicate with the display. The display can also display one of the measurement of the actual angle or corresponding error from the prescribed value, the three-dimensional representation of the angle, average angle per gyration. A memory of the control system 90 can store one of the measurement of the actual angle or corresponding error from the prescribed value, the three-dimensional representation of the angle, average angle per gyration, or any information related to angle or internal angle or external angle, or information relative to passing/failing criteria of target angular information, and average values or information relative to angle.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A gyratory compactor apparatus adapted to interact with a mold that defines a mold axis, said gyratory compactor apparatus comprising:

a frame defining a frame axis and having a first mounting plate and a spaced-apart second mounting plate;

a pivoted support carried by the frame and capable of rotation in at least a first and a second rotational degree of freedom;

a mold-engaging device carried by the pivoted support and having a first carriage plate proximal the pivoted support and a second carriage plate axially spaced-apart from the pivoted support for receiving the mold therebetween, the second carriage plate being laterally moveable relative to the frame axis by rotation of the pivoted support in either of the first or second degrees of freedom; and at least one actuator having a first end carried by the frame and a second end carried by the second carriage plate for imparting lateral translation to the second carriage plate relative to the frame axis, wherein a gyratory internal angle is defined between the frame axis and the mold axis.

2. The gyratory compactor apparatus according to claim 1, wherein the second carriage plate is axially translatable about the mold axis.

3. The gyratory compactor apparatus according to claim 1, wherein the mold-engaging device is slideably carried by the pivoted support.

4. The gyratory compactor apparatus according to claim 3, wherein the mold-engaging device further includes a translation mechanism for providing clamping forces to the mold-engaging device and imparting axial translation of the second carriage plate.

5. The gyratory compactor apparatus according to claim 1, wherein the pivoted support is a gimbal.

6. The gyratory compactor apparatus according to claim 1, further including a ram rod in generally axial alignment with the frame axis for providing rotational movement and compressive forces to the mold about the frame axis.

7. The gyratory compactor apparatus according to claim 6, further including a position sensor in communication with the ram rod.

8. The gyratory compactor apparatus according to claim 6, further including an anti-rotate plate on a distal end of the ram rod and further including a plurality of spaced-apart support beams carried on a first end about a periphery of the anti-rotate plate and carried on a second end at the second mounting plate for providing torsional rigidity to retard torsional strain imparted from rotation of the ram rod.

9. The gyratory compactor apparatus according to claim 1, wherein each actuator of the at least one actuator is a hydraulic actuator.

10. The gyratory compactor apparatus according to claim 1, wherein each actuator of the at least one actuator is independently controlled relative to each other actuator.

11. The gyratory compactor apparatus according to claim 1, further including a displacement measurement device in communication with each actuator of the at least one actuator for measuring displacement of each actuator.

12. The gyratory compactor apparatus according to claim 1, wherein each of the at least one actuators define a longitudinal axis between the first end and the second end of each actuator, and an actuation angle is formed relative to the longitudinal axis of each actuator and the frame axis, and wherein the actuation angle is about 23 degrees.

13. The gyratory compactor apparatus according to claim 1, wherein each actuator of the at least one actuator is carried by the first mounting plate.

14. The gyratory compactor apparatus according to claim 1, wherein the mold is a mold of the type having an elongate cylinder that defines a cavity therein for receiving the sample, and having a peripherally extending flange extending from the cylinder at a first end and a second end thereof.

15. A gyratory compactor apparatus adapted to interact with a mold that defines a mold axis, the gyratory compactor apparatus comprising:
   a frame having a first mounting plate and defining a frame axis extending from the first mounting plate;
   a pivoted support carried by the frame;
   a first carriage plate moveable in response to movement of the pivoted support;
   a second carriage plate spaced-apart from the first carriage plate, the second carriage plate being attached to the first carriage plate by at least one clamping rod extending therebetween;
   a ram rod in general alignment with the second carriage plate for providing compressive and gyratory forces to a mold held between the first and second carriage plates; and
   at least one actuator carried on a first end by the frame and on a second end by the second carriage plate, the actuator being operable to offset the second carriage plate relative to the frame axis such that during gyration of the mold, a gyratory internal angle is defined between the frame axis and the mold axis.

16. The gyratory compactor apparatus according to claim 15, wherein the second carriage plate is axially translatable about the mold axis.

17. The gyratory compactor apparatus according to claim 15, further including a mold-engaging device that is slideably carried by the pivoted support.

18. The gyratory compactor apparatus according to claim 17, wherein the mold engaging device further includes an actuator for imparting axial translation of and providing clamping forces to the second carriage plate.

19. The gyratory compactor apparatus according to claim 15, wherein the pivoted support is a gimbal.

20. The gyratory compactor apparatus according to claim 15, further including a position sensor in communication with the ram rod.

21. The gyratory compactor apparatus according to claim 15, further including an anti-rotate plate on a distal end of the ram rod and further including a plurality of spaced-apart support beams carried on a first end about a periphery of the anti-rotate plate and carried on a second end at the second mounting plate for providing torsional rigidity to retard torsional strain imparted from gyration of the ram rod.

22. The gyratory compactor apparatus according to claim 15, wherein each actuator of the at least one actuator is a hydraulic actuator.

23. The gyratory compactor apparatus according to claim 15, wherein each actuator of the at least one actuator is independently controlled relative to each other actuator.

24. The gyratory compactor apparatus according to claim 15, further including a displacement measurement device in communication with each actuator of the at least one actuator for measuring displacement of each actuator.

25. The gyratory compactor apparatus according to claim 15, wherein each of the at least one actuators define a longitudinal axis between the first end and the second end of each actuator, and an actuation angle is formed relative to the longitudinal axis of each actuator and the frame axis, and wherein the actuation angle is about 23 degrees.

26. The gyratory compactor apparatus according to claim 15, wherein each actuator of the at least one actuator is carried by the first mounting plate.

27. The gyratory compactor apparatus according to claim 15, wherein the mold is a mold of the type having an elongate cylinder that defines a cavity therein for receiving the sample, and having a peripherally extending flange extending from the cylinder at a first end and a second end thereof.

28. A method for testing a sample contained within a mold for a gyratory compactor apparatus, the mold defining a mold axis and the gyratory compactor apparatus having a frame that carries a mold-engaging device having a pivoted support, a first carriage plate moveable in response to movement of the pivoted support, a second carriage plate spaced-apart from the first carriage plate for receiving the mold therebetween, and at least one actuator carried on a first end by the frame and on a second end at the second carriage plate, the method comprising the steps of:
   placing a mold in engagement with the mold-engaging device;
   rotating the mold; and
   imparting lateral displacement of the mold relative to the frame axis by actuation of the at least one actuator to thereby define a gyratory internal angle between the frame axis and the mold axis.

29. The method according to claim 28, wherein the gyratory compactor apparatus further includes a ram rod in general alignment with the mold for compacting the mold, and further including the step of compacting the mold with the ram rod.

30. The method according to claim 29, further including the step of measuring the compaction of the compacted material in the mold.

31. The method according to claim 29, wherein in the step of rotating the mold, the mold is rotated by the ram rod.

32. The method according to claim 28, further including the step of measuring the gyratory internal angle.

33. The method according to claim 32, wherein the measurement of the gyratory internal angle is measured relative to each rotation of the mold.

34. The method according to claim 28, wherein in the step of imparting lateral displacement of the mold relative to the frame axis by actuation of the at least one actuator, the at least one actuator is a hydraulic actuator in communication with a hydraulic source.

* * * * *